US006642245B1

(12) United States Patent
Liotta et al.

(10) Patent No.: US 6,642,245 B1
(45) Date of Patent: *Nov. 4, 2003

(54) ANTIVIRAL ACTIVITY AND RESOLUTION OF 2-HYDROXYMETHYL-5-(5-FLUOROCYTOSIN-1-YL)-1,3-OXATHIOLANE

(75) Inventors: Dennis C. Liotta, Stone Mountain, GA (US); Raymond F. Schinazi, Decatur, GA (US); Woo-Baeg Choi, North Brunswick, NJ (US)

(73) Assignee: Emory University, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/475,339

(22) Filed: Jun. 7, 1995

Related U.S. Application Data

(63) Continuation of application No. 07/831,153, filed on Feb. 12, 1992, now abandoned, and a continuation-in-part of application No. 07/736,089, filed on Jul. 26, 1991, now abandoned, which is a continuation-in-part of application No. 07/659,760, filed on Feb. 22, 1991, now Pat. No. 5,210,085, which is a continuation-in-part of application No. 07/473,318, filed on Feb. 1, 1990, now Pat. No. 5,204,466.

(51) Int. Cl.[7] .................... A61K 31/506; C07D 411/04
(52) U.S. Cl. .................. 514/274; 514/86; 544/243; 544/317
(58) Field of Search .................. 514/86, 274

(56) References Cited

U.S. PATENT DOCUMENTS

| | | | |
|---|---|---|---|
| 4,000,137 A | 12/1976 | Dvonch et al. | 260/252 |
| 4,336,381 A | 6/1982 | Nagata et al. | 544/313 |
| 4,861,759 A | 8/1989 | Hiroaki et al. | 514/46 |
| 4,879,277 A | 11/1989 | Mitsuya et al. | 514/49 |
| 4,900,828 A | 2/1990 | Belica et al. | 544/243 |
| 4,916,122 A | 4/1990 | Chu et al. | 514/50 |
| 4,963,533 A | 10/1990 | de Clercq et al. | 514/49 |
| 5,011,774 A | 4/1991 | Farina et al. | 435/87 |
| 5,041,449 A | 8/1991 | Belleau et al. | 514/274 |
| 5,047,407 A | 9/1991 | Belleau et al. | 514/274 |
| 5,059,690 A | 10/1991 | Zahler et al. | 544/276 |
| 5,071,983 A | 12/1991 | Koszalka et al. | 544/243 |
| 5,179,104 A | 1/1993 | Chu et al. | 544/310 |
| 5,185,437 A | 2/1993 | Koszalka et al. | 536/24 |
| 5,204,466 A | 4/1993 | Liotta et al. | 544/317 |
| 5,210,085 A | 5/1993 | Liotta et al. | 514/274 |
| 5,234,913 A | 8/1993 | Furman, Jr. et al. | 514/49 |
| 5,248,776 A | 9/1993 | Chu et al. | 544/310 |
| 5,270,315 A | 12/1993 | Belleau et al. | 514/262 |
| 5,276,151 A | 1/1994 | Liotta | 544/317 |
| 5,444,063 A | 8/1995 | Schinazi | 514/262 |
| 5,466,806 A | 11/1995 | Belleau et al. | 544/310 |
| 5,486,520 A | 1/1996 | Belleau et al. | 514/274 |
| 5,532,246 A | 7/1996 | Belleau et al. | 514/274 |
| 5,539,116 A | 7/1996 | Liotta et al. | 544/317 |
| 5,587,480 A | 12/1996 | Belleau et al. | 544/310 |
| 5,618,820 A * | 4/1997 | Dionne | 514/274 |

FOREIGN PATENT DOCUMENTS

| | | |
|---|---|---|
| AU | 73004/91 | 8/1991 |
| AU | 665187 | 2/1992 |
| AU | 630913 | 9/1992 |
| EP | 0 217 580 | 4/1987 |
| EP | 0 337 713 | 10/1988 |
| EP | 350 811 | 1/1990 |
| EP | 0 375 329 | 1/1990 |
| EP | 357 009 | 3/1990 |
| EP | 0 361 831 | 4/1990 |
| EP | 0 382 526 | 6/1990 |
| EP | 0 433 898 | 8/1990 |
| EP | 421 636 | 4/1991 |
| EP | 0 494 119 | 7/1992 |
| EP | 0 515 144 | 11/1992 |
| EP | 0 515 156 | 11/1992 |
| EP | 0 515 157 | 11/1992 |
| EP | 0 526 253 | 2/1993 |
| JP | 2-69469 | 3/1990 |
| JP | 2-69476 | 3/1990 |
| JP | 07109221 | 4/1995 |
| NL | 8901258 | 12/1990 |
| NL | 238017 | 6/1994 |
| WO | WO88/07532 | 10/1988 |
| WO | WO90/12023 | 10/1990 |
| WO | WO91/11186 | 8/1991 |
| WO | WO91/17159 | 11/1991 |
| WO | WO92/08727 | 5/1992 |
| WO | WO92/10496 | 6/1992 |
| WO | WO92/10497 | 6/1992 |
| WO | WO92/14729 | 9/1992 |
| WO | WO92/14743 | 9/1992 |
| WO | WO92/15308 | 9/1992 |
| WO | WO92/15309 | 9/1992 |
| WO | WO92/18517 | 10/1992 |
| WO | WO92/21676 | 12/1992 |
| WO | WO94/04154 | 3/1994 |
| WO | WO94/09793 | 5/1994 |
| WO | WO94/14802 | 7/1994 |

OTHER PUBLICATIONS

Abobo, et al., "Pharmacokinetics of 2',3'–Dideoxy–5–fluoro–3'–thiacytidine in Rats," *J. of Pharmaceutical Sciences*, 83(1):96–99 (1994).

(List continued on next page.)

Primary Examiner—Richard L. Raymond
(74) Attorney, Agent, or Firm—King & Spalding, LLP; Sherry & Knowles, Esq.

(57) ABSTRACT

A method and composition for the treatment of HIV and HBV infections in humans is disclosed that includes administering an effective amount of 2-hydroxymethyl-5-(5-fluorocytosin-1-yl)-1,3-oxathiolane, a pharmaceutically acceptable derivative thereof, including a 5' or $N^4$ alkylated or acylated derivative, or a pharmaceutically acceptable salt thereof, in a pharmaceutically acceptable carrier.

A process for the resolution of a racemic mixture of nucleoside enantiomers is also disclosed that includes the step of exposing the racemic mixture to an enzyme that preferentially catalyzes a reaction in one of the enantiomers.

22 Claims, 6 Drawing Sheets

OTHER PUBLICATIONS

Agranat and Biedermann, "Intellectual Property and Chirality: Patentability of Enantiomers of Racemic Drugs in a Racemic Switch Scenario," $8^{th}$ *Chirality Conference, Edinburgh*, UK (Jul. 2, 1996).

Balzarini, J., et al., "Potent and Selective Anti–HTLV–III/LAV Activity of 2,', 3'–Dideoxycytidine, the 2', 3'–Unsaturated Derivative of 2', 3'–Dideoxycytidine," *Biochemical and Biophysical Research Communications*, 140(2): 735–742 (1986).

Baschang, et al., "The enantiomers of 1.beta.–adenyl–2.alpha.–hydroxy–3.beta.–(hydroxymethyl) cyclobutane," *Tetrahedron:Asymmetry*, 3(2): 193–6 (1992).

Belleau, B., et al., "Design and Activity of a Novel Class of Nucleoside Analogs Effective Against HIV–1,", *International Conference on AIDS*, Montreal, Quebec, Canada, Jun. 4–9, 1989.

Borthwick, et al., "Synthesis and Enyzmatic Resolution of Carbocyclic 2'–Ara–Fluoro–Guanosine: A Potent New Anti– Herpetic Agent," *J. Chem. Soc. Commun.*, vol. 10, pp. 656–658 (1988).

Carter, et al., "Activities of (–)–Carbovir and 3'–Azido–3'–Deoxythymidine Against Human Immunodeficiency Virus In Vitro," *Antimicrobial Agents and Chemotherapy*, 34(6):1297–1300 (1990).

Chang, Chien–Neng, et al., "Deoxycytidine Deaminase–resistant Steroisomer Is the Active Form of (+)–2', '–Dideoxy–3'–thiacytidine in the Inhibition of Hepatitis B Virus Replication," *The Journal of Biological Chemistry*, 267(20):13938–13942 (1992).

Chu, C.K., et al., "An Efficient Total Synthesis of 3'–Azido–3'–Deoxythiymidine (AZT) and 3'–Azido–2', 3'–Dideoxyuridine (AZDDU, CS–87) from D–Mannitol," *Tetrahedron Lett.*, 29(42):5349–5352 (1988).

Chu, et al., "Comparative Activity of 2', 3'–Saturated and Unsaturated Pyrimidine and Purine Nucleosides Against Human Immunodeficiency Virus Type 1 in Peripheral Blood Mononuclear Cells," *Biochem. Pharm.*, 37(19):3543–3548 (1988).

Chu, et al., "Structure–Activity Relationships of Pyrimidine Nucleosides as Antiviral Agents for Human Immunodeficiency Virus Type 1 in Peripheral Blood Mononuclear Cells," *J. Med. Chem.*, 32:612(1989).

Condreay, et al., "Evaluation of the Potent Anti–Hepatitis B Virus Agent(–) *cis*–5–Fluoro–1–[2–(Hydroxymethyl)–1,3–Oxathiolan–5–yl]Cytosine in a Novel in Vivo Model," *Antimicrobial Agents and Chemotherapy*, 616–619 (1992).

Connolly and Hammer, "Minireview: Antiretroviral Therapy: Reverse Transcriptase Inhibition," *Antimicrobial Agents and Chemotherapy*, 36(2):245–254 (1992).

Cretton, E., et al., "Catabolism of 3'–Azido–3'–Dexoythymidine in Hepatocytes and Liver Microsomes, with Evidence of Formation of 3'–Amino–3'–Deoxythymidine, a Highly Toxic Catabolite for Human Bone Marrow Cells," *Molecuilar Pharmacology*, 39:258–266 (1991).

Cretton, E., et al., "Pharmokinetics of 3'–Azido–3'–Deoxythymidine and its Catabolites and Interactions with Probenecid in Rhesus Monkeys," *Antimicrobial Agents and Chemotherapy*, 35(5):801–807 (1991).

Doong, Shin–Lian., et al., "Inhibition of the Replication of Hepatitis B Virus in vitro by 2',3'–Dideoxy–3'–Thiacytidine and Related Analogues," *Natl. Acad. Sci. USA*, 88:8495–8499 (1991).

Feorino, et al., "Prevention of activation of HIV–1 by antiviral agents in OM 10.1 cells," *Antiviral Chem. & Chemotherapy*, 4(1):55–63 (1993).

Frick, et al., "Pharmacokinetics, Oral Bioavailability, and Metabolic Disposition in Rats of (–)–cis–5–Fluoro–1–[2–(Hydroxymethyl)–1,3–Oxathiolan–5–yl] Cytosine, a Nucleoside Analog Active against Human Immunodeficiency Virus and Hepatitis B Virus," *Antimicrobial Agents and Chemotherapy*, 37(11):2285–2292 (1993).

Furman, et al., "The Anti–Hepatitis B Virus Activities, Cytotoxicities, and Anabolic Profiles of the (–) and (+) Enantiomers of cis–5–Fluoro–1–[2–(Hydromethyl)–1,3–Oxthiolane–5–yl]Cytosine," *antimicrobial Agents and Chemotherapy*, 36(12):2686–2692 (1992).

Herdewijn, et al., "Resolution of Aristeromycin Enantiomers," *J. Med. Chem.*, 1985, vol. 28, 1385–1386.

Hoong, et al., "Enzyme–Mediated Enatioselective Preparation of Pure Enantiomers of the Antiviral Agent 2', 3'–Dideoxy–5–fluoro–thiacytidine (FTC) and Related Compounds," *J. Org. Chem.*, 57:5563–5565 (1992).

Ito, et al., "Chirally Selective Synthesis of Sugar Moiety of Nucleosides by Chemicoenzymatic Approach: L–and D–Riboses, Showdomycin, and Cordycepin," *J. Am. Chem. Soc.*, 103:6739–6741 (1981).

Jansen, et al., "High–Capacity In Vitro Assessment of Anti–Hepatitis B Virus Compound Selectivity by a Virion–Specific Polymerase Chain Reaction Assay," *Antimicrobial Agents and Chemotherapy*, 441–447 (1993).

Jeong, L., et al., "Asymmetric Synthesis and Biological Evaluation of β–L–(2R,5S)–and a–L(2R–5R)–1,3–Oxathiolane–Pyrimidine and –Purine Nucleosides and Potential Anti–HIV Agents," *J. Med. Chem.*, 36(2):181–195 (1993).

Krenitsky, T.A., et al., "3'–Amino–2',3'–Dideoxyribonucleosides of Some Pyrimidines: Synthesis and Biological Activities," *J. Med. Chem.*, vol. 26 (1983).

Krenitsky, et al., "An Enzymic Synthesis of Purine D–arabinonucleosides," *Carbohydrate Research*, 97:139–146 (1981).

Lin, et al., "Potent and Selective In Vitro Activity of 3–Deoxythmindine–2–Ene–(3'–Deoxy–2',3'–Didehydrothymidine) Against Human Immunodeficiency Virus," *Biochem. Pharm.*, 36(17):2713–2718 (1987).

Mahmoudian, et al., "Enzymatic Production of Optically Pure (2'R–cis)–2'–deoxy–3'–thiacytidine (3TC, Lamivudine): A Potent Anti–HIV Agent," *Enzyme Microb. Technol.*, Sep. 1993, vol. 15, 749–755, published by the Glaxo Group Research.

Mitsuya, H., et al., 3'–Azido–3'–Deoxythymidine (BW A 509U): An Antiviral Agent that Inhibits the Infectivity and Cytopathic Effect of Human T–Lymphotropic Virus Type III/Lymphadenopathy–Associated Virus *In Vitro, Proc. Natl. Acad. Sci., USA*, 82:7096–7100 (1985).

Mitsuya, H., et al., "Molecular Targets for AIDS Therapy," *Science*, vol. 249, pp. 1533–1544 (1990).

Mitsuya, H., et al., "Rapid in Vitro Systems for Assessing Activity of Agents Against HTLV–III/LAV," *AIDS: Modern Concepts and Therapeutic Challenges*, S. Broder, Ed. pp. 303–333, Marcel Dekker: New York, (1987).

Norbeck, D., et al., "A New 2',3'–Dideoxynucleoside Prototype with In Vitro Activity Against HIV," *Tetrahedron Lett.*, 30(46):6263–6266 (1989).

Ohno, et al., "Synthetic Studies on Biologically Active Natural Products by a Chemicoenzymatic Approach," *Tet. Letters*, 40:145–152 (1984).

Okabe, M., et al., "Synthesis of the Dideoxynucleosides ddC and CNT from Glutamic Acid, Ribonolactone, and Pyrimidine Bases," *J. Org. Chem.*, 53(20):4780–4786 (1988).

Paff, et al., "Intracellular Metabolism of (−)-and (+)-cis-5-Fluoro-1-[2-Hydroxymethyl)-1, 3-Oxathiolan-5-yl]Cytosine in HepG2 Derivative 2.2.15 (Subclone P5A)Cells," *Antimicrobial Agents and Chemotherapy*, 1230–1238 (1994).

Pirkle and Pochansky, "Chiral Stationary Phases for the Direct LC Separation of Enantiomers," *Advances in Chromatography*, Giddings, J.C., Grushka, E., Brown, P.R., eds.: Marcel Dekker: New York, 1987; vol. 27, Chap. 3, pp. 73–127.

Richman, D. D., et al., "The Toxicity of Azidothymidine (AZT) in the Treatment of Patients with AIDS and AIDS-Related Complex," *N. Eng. J. Med.*, 317(4):192–197 (1987).

Roberts, et al., "Enzymic Resolution of cis–and trans–4–hydroxycyclopent–2–enylmethanol..." *J. Chem. Soc.*, Perkin Trans. 1, (10):2605–7 (1991).

Saari, et al., "Synthesis and Evaluation of 2–Pyridinone Derivatives as HIV–1–Specific Reverse Transcriptase Inhibitors, 2. Analogues of 3–Aminopyridin–2(1H)–one," *J. Med. Chem.*, 35:3792–3802 (1992).

Satsumabayashi, S. et al., "The Synthesis of 1,3–Oxathiolane–5–one Derivatives," *Bull, Chem. Soc. Japan*, 45:913–915 (1972).

Saunders, "Non–Nucleoside Inhibitors of HIV Reverse Transcriptase: Screening Successes–Clinical Failures," *Drug Design and Discovery*, 8:255–263 (1992).

Schinazi, R.F., et al., "Actvities of the Four Optical Isomers of 2',3'–Dideoxy–3'–Thiacytidine (BCH–189) against Human Immunodeficiency Virus Type 1 in Human Lymphocytes," *Antimicrobial Agents and Chemotherapy* 36(3):672–676 (1992).

Schinazi, R.F., et al., "Insights into HIV Chemotherapy, "*AIDS Research and Human Retroviruses* 8(6):963–990 (1992).

Schinazi, R.F., et al., "Pharmacokinetics and Metabolism of Racemic 2', 3'–Dideoxy–5–Fluoro–3'–Thiacytidine in Rhesus Monkeys," *Antimicrobial Agents and Chemotherapy* 36(11):2432–2438 (1992).

Schinazi, R.F., et al., "Selective Inhibition of Human Immunodeficiency Viruses by Racemates and Enantiomers of cis–5–Fluoro–1–[2–(Hydroxymethyl)–1, 3–Oxathiolan–5–yl]Cytosine," *Antimicrobial Agents and Chemotherapy* 36(11):2423–2431 (1992).

Schinazi, R.F., et al., "Substrate Specificity of *Escherichia Coli* Thymidine Phosphorylase for Pyrimidine Nucleoside with an Anti–Human Immunodeficiency Virus Activity," *Biochemical Pharmacology* 44(2):199–204 (1992).

Secrist, et al., "Resolution of Racemic Carbocyclic Analogues of Purine Nucleosides Through the Action of Adenosine Deaminase Antiviral Activity of the Carbocyclic 2'–Deoxyguanosine Enantiomers," *J. Med. Chem.* , vol. 30, pp. 746–749 (1987).

Shewach, et al., "Affinity of the antiviral enantiomers of oxathiolane cytosine nucleosides for human 2'–deoxycytidine kinase," *Biochem. Pharmacol.*, 45(7):1540–1543 (1993).

Sterzycki, R.Z., et al., "Synthesis and anti–HIV activity of several 2'–fluoro–containing pyrimidine nucleosides," *J. Med. Chem.*, 33(8):2150–2157 (1990).

Storer, R., et al., "The Resolution and Absolute Stereochemistry of the Enantiomeris of cis–1–2–(Hydromethyl)–1, 3–Oxathiolan–5–yl)cytosine (BCH198): Equipotent Anti–HIV Agents," *Nucleosides & Nucleotides*, 12(2):225–236 (1993).

van Roey, et al., "Solid–State Conformation of Anti–Human Immnosudeficiency Virus Type–1 Agents: Crystal Structures of Three 3'–Azido–3'–deoxythymidine Analogues," *J. Am. Chem. Soc.*, 110:2277–2782 (1988).

Vorbrüggen, et al., "Nucleoside Synthesis with Trimethylsiyl Triflate and Perchlorate as Catalysts," *Chem. Ber.*, 114:1234–1255 (1981).

Wilson, et al., "The 5'–Triphosphates of the (1) and (+) Enantiomers of cis–5–Fluoro–1–[2–(Hydroxymethyl)–1, 3–Oxathiolane–5–yl]Cytosine Equally Inhibit Human Immunodeficiency Virus Type 1 Reverse Transcriptase," *Antimicrob. Agents and Chemother.*, 37(8):1720–1722 (1993).

Wilson, L.J., et al., "A General Method for Controlling Glycosylation Stereochemistry in the Synthesis of 2'–Deoxyribose Nucleosides," *Tetrahedron Lett.*, 31(13):1815–1818 (1990).

Wilson, L.J., et al., "The Synthesis and Anti–HIV Activity of Pyrimidine Dioxolanyl Nucleosides," *Bioorganic & Medicinal Chemistry Letters*, 3(2):169–174 (1993).

Winslow, et al., "*In vitro* susceptibility of clinical isolates of HIV–1 to XM323, a non–peptidyl HIV protease inhibitor," *AIDS*, 8:753–756 (1994).

Zhu, Zhou, et al., "Cellular Metabolism of 3'–Azido–2', 3'–Dideoxyuridine with Formation of 5'–O–Diphophoshexase Derivatives by Previously Unrecognized Metabolic Pathways of 2'–Deoxyuridine Analogs," *Molecular Pharmacology*, 0:929–938 (1990).

Journal of Acquired Immune Deficiency Syndromes, (Raven Press, Pubisher), vol. 6 (1993).

* cited by examiner

ANTIVIRAL ACTIVITY AND RESOLUTION OF 2-HYDROXYMETHYL-5-(5-FLUOROCYTOSIN-1-YL)-1,3-OXATHIOLANE

This application is a Continuation application of U.S. Ser. No. 07/831,153, filed on Feb. 12, 1992 now abandoned, by Dennis C. Liotta, Raymond F. Schinazi, and Woo-Baeg Choi for "Antiviral Activity and Resolution of 2-Hydroxymethyl-5(5-Fluorocytosin-1-yl)-1,3-Oxathiolane" which is a continuation-in-part application of (1) U.S. Ser. No. 07/659,760, now U.S. Pat. No. 5,210,085, entitled "Method for the Synthesis, Compositions and Use of 2'-Deoxy-5-Fluoro-3'-Thiacytidine and Related Compounds", filed on Feb. 22, 1991, by Dennis C. Liotta, Raymond F. Schinazi, and Woo-Baeg Choi, which is a continuation in part application of U.S. Ser. No. 07/473,318, now U.S. Pat. No. 5,204,466, entitled "Method and Compositions for the Synthesis of BCH-189 and Related Compounds", filed on Feb. 1, 1990, by Dennis C. Liotta and Woo-Baeg Choi and, (2) a continuation-in-part of U.S. Ser. No. 07/736,089, now abandoned, entitled "Method of Resolution and Antiviral Activity of 1,3-Oxathiolane Nucleoside Enantiomers" filed on Jul. 26, 1991, by Dennis C. Liotta, Raymond F. Schinazi, and Woo-Baeg Choi, which is a continuation-in-part of U.S. Ser. No. 07/659,760, now U.S. Pat. No. 5,210,085, referenced above.

The U.S. Government has rights in this invention arising out of the partial funding of work leading to this invention through the National Institutes of Health Grant Nos. AI-26055, AI-28731, NIH 5-21935, as well as a Veteran's Administration Merit Review Award.

BACKGROUND OF THE INVENTION

This invention is in the area of biologically active nucleosides, and specifically includes antiviral compositions that include 2-hydroxymethyl-5-(5-fluorocytosin-1-yl)-1,3-oxathiolane ("FTC"), its physiologically acceptable derivative, or physiologically acceptable salt, and a method for the resolution and use of the (−)-β-L and (+)-β-D enantiomers of FTC.

In 1981, acquired immune deficiency syndrome (AIDS) was identified as a disease that severely compromises the human immune system, and that almost without exception leads to death. In 1983, the etiological cause of AIDS was determined to be the human immunodeficiency virus (HIV). By December of 1990, the World Health Organization estimated that between 8 and 10 million people worldwide were infected with HIV, and of that number, between 1,000,000 and 1,400,000 were in the U.S.

In 1985, it was reported that the synthetic nucleoside 3'-azido-3'-deoxythymidine (AZT) inhibits the replication of human immunodeficiency virus. Since then, a number of other synthetic nucleosides, including 2',3'-dideoxyinosine (DDI), 2',3'-dideoxycytidine (DDC), 3'-fluoro-3'-deoxythymidine (FLT), and 2',3'-dideoxy-2',3'-didehydrothymidine (D4T), have been proven to be effective against HIV. A number of other 2',3'-dideoxynucleosides have been demonstrated to inhibit the growth of a variety of viruses in vitro. It appears that, after cellular phosphorylation to the 5'-triphosphate by cellular kinases, these synthetic nucleosides are incorporated into a growing strand of viral DNA, causing chain termination due to the absence of the 3'-hydroxyl group.

The success of various 2',3'-dideoxynucleosides in inhibiting the replication of HIV in vivo or in vitro has led a number of researchers to design and test nucleosides that substitute a heteroatom for the carbon atom at the 3'-position of the nucleoside. Norbeck, et al., disclose that (±)-1-[(2β, 4β)-2-(hydroxymethyl)-4-dioxolanyl]thymine (referred to as (±)-dioxolane-T) exhibits a modest activity against HIV ($EC_{50}$ of 20 μm in ATH8 cells), and is not toxic to uninfected control cells at a concentration of 200 μM. *Tetrahedron Letters* 30 (46), 6246, (1989). European Patent Application Publication No. 0 337 713 and U.S. Pat. No. 5,041,449, assigned to IAF BioChem International, Inc., disclose 2-substituted-4-substituted-1,3-dioxolanes that exhibit antiviral activity.

U.S. Pat. No. 5,047,407 and European Patent Application Publication No. 0 382 526, also assigned to IAF Biochem International, Inc. disclose a number of 2-substituted-5-substituted-1,3-oxathiolane nucleosides with antiviral activity, and specifically report that the racemic mixture (about the C4'-position) of the C1'-β isomer of 2-hydroxymethyl-5-(cytosin-1-yl)-1,3-oxathiolane (referred to below as (±)-BCH-189) has approximately the same activity against HIV as AZT, and no cellular toxicity at the tested levels. (±)-BCH-189 has also been found to inhibit the replication of AZT-resistant HIV isolates in vitro from patients who have been treated with AZT for longer than 36 weeks.

Another virus that causes a serious human health problem is the hepatitis B virus (referred to below as "HBV"). HBV is second only to tobacco as a cause of human cancer. The mechanism by which HBV induces cancer is unknown, although it is postulated that it may directly trigger tumor development, or indirectly trigger tumor development through chronic inflammation, cirrhosis, and cell regeneration associated with the infection.

After a two to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed.

Patients typically recover from acute hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and worldwide, almost 300 million carriers. Chronic persistent hepatitis can cause fatigue, cirrhosis of the liver, and hepatocellular carcinoma, a primary liver cancer.

In western industrialized countries, high risk groups for HBV infection include those in contact with HBV carriers or their blood samples. The epidemiology of HBV is very similar to that of acquired immune deficiency syndrome, which accounts for why HBV infection is common among patients with AIDS or AIDS-related complex. However, HBV is more contagious than HIV.

A human serum-derived vaccine has been developed to immunize patients against HBV. While it has been found effective, production of the vaccine is troublesome because the supply of human serum from chronic carriers is limited, and the purification procedure is long and expensive. Further, each batch of vaccine prepared from different serum must be tested in chimpanzees to ensure safety. Vaccines have also been produced through genetic engineering. Daily treatments with a-interferon, a genetically engineered protein, has also shown promise. However, to date there is no known pharmaceutical agent that effectively inhibits the replication of the virus.

To market a nucleoside for pharmaceutical purposes, it must not only be efficacious with low toxicity, it must also be cost effective to manufacture. An extensive amount of research and development has been directed toward new, low cost processes for large scale nucleoside production. 2',3'-Dideoxynucleosides are currently prepared by either of two routes: derivatization of an intact nucleoside or condensation of a derivatized sugar moiety with a heterocyclic base. Although there are numerous disadvantages associated with obtaining new nucleoside analogues by modifying intact nucleosides, a major advantage of this approach is that the appropriate absolute stereochemistry has already been set by nature. However, this approach cannot be used in the production of nucleosides that contain either nonnaturally occurring bases or nonnaturally occurring carbohydrate moieties (and which therefore are not prepared from intact nucleosides), such as 1,3-oxathiolane nucleosides and 1,3-dioxolane nucleosides.

When condensing a carbohydrate or carbohydrate-like moiety with a heterocyclic base-to form a synthetic nucleoside, a nucleoside is produced that has two chiral centers (at the C1'and C4'-positions), and thus exists as a diastereomeric pair. Each diastereomer exists as a set of enantiomers. Therefore, the product is a mixture of four enantiomers.

It is often found that nucleosides with nonnaturally-occurring stereochemistry in either the C1'or the C4'-positions are less active than the same nucleoside with the stereochemistry as set by nature. For example, Carter, et al., have reported that the concentration of the (−)-enantiomer of carbovir (2',3'-didehydro-2',3'-dideoxyguanosine) in cell culture required to reduce the reverse transcriptase activity by 50% ($EC_{50}$) is 0.8 $\mu$M, whereas the $EC_{50}$ for the (+)-enantiomer of carbovir is greater than 60 $\mu$M. *Antimicrobial Agents and Chemotherapy*, 34:6, 1297–1300 (June 1990).

PCT International Publication No. WO 91/11186 discloses that 1,3-oxathiolane nucleosides can be prepared with high diastereoselectivity (high percentage of nucleoside with a β configuration of the bond from the C1'-carbon to the heterocyclic base) by careful selection of the Lewis acid used in the condensation process. It was discovered that condensation of a 1,3-oxathiolane nucleoside with a base occurs with almost complete β-stereospecificity when stannic chloride is used as the condensation catalyst. Other Lewis acids provide low (or no) C1'-β selectivity or simply fail to catalyze the reactions.

In light of the fact that acquired immune deficiency syndrome, AIDS-related complex, and hepatitis B virus have reached epidemic levels worldwide, and have tragic effects on the infected patient, there remains a strong need to provide new effective pharmaceutical agents to treat these diseases that have low toxicity to the host.

There is also a need to provide a cost effective, commercially viable method to produce pharmaceutically important nucleosides, and specifically attain β-stereospecificity in the C4'-position of synthetic nucleosides prepared by condensing a carbohydrate-like moiety with a base.

Therefore, it is an object of the present invention to provide a method and composition for the treatment of human patients infected with HIV.

It is another object of the present invention to provide a method and composition for the treatment of human patients or other host animals infected with HBV.

It is still another object of the present invention to provide enantiomerically enriched 1,3-oxathiolane nucleosides.

It is still another object of the present invention to provide a method for the resolution of C4'-enantiomers of 1,3-oxathiolane nucleosides.

SUMMARY OF THE INVENTION

A method and composition for the treatment of HIV and HBV infections in humans and other host animals is disclosed that includes administering an effective amount of 2-hydroxymethyl-5-(5-fluorocytosin-1-yl)-1,3-oxathiolane, a pharmaceutically acceptable derivative thereof, including a 5'or $N^4$ alkylated or acylated derivative, or a pharmaceutically acceptable salt thereof, in a pharmaceutically acceptable carrier.

It has been discovered that 2-hydroxymethyl-5-(5-fluorocytosin-1-yl)-1,3-oxathiolane ("FTC"), exhibits surprisingly high activity against human immunodeficiency virus with very low host cell toxicity. It has also been discovered that FTC exhibits very significant activity against HBV, and therefore can be used to treat patients who have a variety of illnesses associated with HBV infection.

Toxicity and pharmacokinetic studies confirm the usefulness of FTC as an antiviral agent for pharmaceutical administration. FTC and its enantiomers are nontoxic to peripheral human bone marrow cells at concentrations up to 50 $\mu$M and other cell lines at concentrations up to 200 $\mu$M. FTC-TP is a major intracellular metabolite in PBMC and HepG2 cells. FTC-TP competitively inhibits HIV-1 reverse transcriptase (RT) with a $K_i$, of 0.2 $\mu$M using a poly(I)oligo(dC) template-primer. Using sequencing analysis, FTC-TP can be shown to be a potent DNA chain terminator when HIV-RT is used (C-stops).

Chronic treatment with FTC is not toxic to rodents, even at oral doses of 85 mg/kg per day for at least two months. The pharmacokinetics of FTC in rhesus monkeys indicates high oral bioavailability (approximately 73±6%) and a plasma terminal half life of approximately 1.34±0.18 (mean of oral and I.V. administration).

A process for the resolution of a racemic mixture of nucleoside enantiomers, including the racemic mixture of FTC, is also disclosed that includes the step of exposing the racemic mixture to an enzyme that preferentially catalyzes a reaction in one of the enantiomers. The process can be used to resolve a wide variety of nucleosides, including pyrimidine and purine nucleosides that are optionally substituted in the carbohydrate moiety or base moiety. The process can also be used to resolve nucleoside derivatives that contain additional heteroatoms in the carbohydrate moiety, for example, (±)-FTC and (±)-BCH-189. The resolution of nucleosides can be performed on large scale at moderate cost.

Using methods described herein, FTC was resolved into its (+)-β-D and (−)-β-L enantiomers. The (−)-β-L-enantiomer appears to be more potent that the (+)-β-D-enantiomer against HIV, HBV, and SIV. The (+)-enantiomer of FTC is also active against HIV, HBV, and SIV.

DETAILED DESCRIPTION OF THE INVENTION

Figure 1:
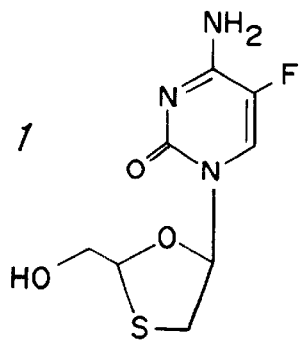
FIG. 1 is an illustration of the chemical structure of 2-hydroxymethyl-5-(5-fluorocytosin-1-yl)-1,3-oxathiolane ("FTC").

As used herein, the term "enantiomerically enriched nucleoside" refers to a nucleoside composition that includes at least 95% of a single enantiomer of that nucleoside.

As used herein, the term FTC refers to 2-hydroxymethyl-5-(5-fluorocytosin-1-yl)-1,3-oxathiolane (the racemic form or enantiomers), also referred to as 2'-deoxy-5-fluoro-3'-thiacytidine.

As used herein, the term (±)-FTC refers to (±)-β-D,L-2-hydroxymethyl-5-(5-fluorocytosin-1-yl)-1, 3-oxathiolane.

As used herein, the term (−)-FTC refers to (−)-β-L-2-hydroxymethyl-5-(5-fluorocytosin-1-yl)-1, 3-oxathiolane.

As used herein, the term (+)-FTC refers to (+)-β-D-2-hydroxymethyl-5-(5-fluorocytosin-1-yl)-1, 3-oxathiolane.

As used herein, the terms FTC-MP, FTC-DP, and FTC-TP refer to the monophosphate, diphosphate, and triphosphate of FTC, respectively.

As used herein, the term BCH-189 refers to 2-hydroxymethyl-5-(cytosin-1-yl)-1,3-oxathiolane.

As used herein, the term "preferential enzyme catalysis" refers to catalysis by an enzyme that favors one substrate over another.

As used herein, a leaving group means a functional group that forms an incipient carbonation when it separates from the molecule that it is attached to.

The invention as disclosed herein is a method and composition for the treatment of HIV and HBV infections, and other viruses replicating in like manner, in humans or other host animals, that includes administering an effective amount of the (±)-β-D,L, the (−)-β-L or (+)-β-D enantiomer of 2-hydroxymethyl-5-(5-fluorocytosin-1-yl)-1,3-oxathiolane, a pharmaceutically acceptable derivative, including a 5' or $N^4$ alkylated or acylated derivative, or a pharmaceutically acceptable salt thereof, in a pharmaceutically acceptable carrier. As shown below, the compounds of this invention either possess antiretroviral activity, such as anti-HIV-1, anti-HIV-2 and anti-simian immunodeficiency virus (anti-SIV) activity, themselves or are metabolized to a compound that exhibits antiretroviral activity.

FTC and its pharmaceutically acceptable derivatives or salts or pharmaceutically acceptable formulations containing these compounds are useful in the prevention and treatment of HIV infections and other related conditions such as AIDS-related complex (ARC), persistent generalized lymphadenopathy (PGL), AIDS-related neurological conditions, anti-HIV antibody positive and HIV-positive conditions, Kaposi's sarcoma, thrombocytopenia purpurea and opportunistic infections. In addition, these compounds or formulations can be used prophylactically to prevent or retard the progression of clinical illness in individuals who are anti-HIV antibody or HIV-antigen positive or who have been exposed to HIV.

FTC and its pharmaceutically acceptable derivatives or pharmaceutically acceptable formulations containing these compounds are also useful in the prevention and treatment of HBV infections and other related conditions such as anti-HBV antibody positive and HBV-positive conditions, chronic liver inflammation caused by HBV, cirrhosis, acute hepatitis, fulminant hepatitis, chronic persistant hepatitis, and fatigue. These compounds or formulations can also be used prophylactically to prevent or retard the progression of clinical illness in individuals who are anti-HBV antibody or HBV-antigen positive or who have been exposed to HBV.

FTC can be converted into a pharmaceutically acceptable ester by reaction with an appropriate esterifying agent, for example, an acid halide or anhydride. FTC or its pharmaceutically acceptable derivative can be converted into a pharmaceutically acceptable salt thereof in a conventional manner, for example, by treatment with an appropriate base. The ester or salt of FTC can be converted into FTC, for example, by hydrolysis.

In summary, the present invention includes the following features:

(a) (±)-β-D,L-2-hydroxymethyl-5-(5-fluorocytosin-1-yl)-1, 3-oxathioiane and pharmaceutically acceptable derivatives and salts thereof;

(b) (−)-β-L-2-hydroxymethyl-5-(5-fluorocytosin-1-yl)-1, 3-oxathiolane and pharmaceutically acceptable derivatives and salts thereof;

(c) (+)-βD-2-hydroxymethyl-5-(5-fluorocytosin-1-yl)-1, 3-oxathiolane and pharmaceutically acceptable derivatives and salts thereof;

(d) (±)-β-D,L-2-hydroxymethyl-5-(5-fluorocytosin-1-yl)-1, 3-oxathiolanei its (−) and (+) enantiomers, and pharmaceutically acceptable derivatives and salts thereof for use in medical therapy, for example for the treatment or prophylaxis of a HIV or HBV infection;

(e) use of (±)-β-D,L-2-hydroxymethyl-5-(5-fluorocytosin-1-yl)-1, 3-oxathiolane, its (−) and (+)

enantiomers, and pharmaceutically acceptable derivatives and salts thereof in the manufacture of a medicament for treatment of a HIV or HBV infection;

(f) pharmaceutical formulations comprising (±)-β-D,L-2-hydroxymethyl-5-(5-fluorocytosin-1-yl)-1,3-oxathiolane, its (−) or (+) enantiomer, or a pharmaceutically acceptable derivative or salt thereof together with a pharmaceutically acceptable carrier or diluent;

(g) a process for the preparation of 2-hydroxymethyl-5-(5-fluorocytosin-1-yl)-1,3-oxathiolane which comprises:

(i) reacting optionally protected 5-fluorocytosine with a 1,3-oxathiolane of formula A

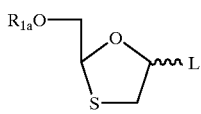

wherein $R_{1a}$ is hydrogen or a hydroxyl protecting group, including an acyl group, and L is a leaving group; and optionally removing any hydroxyl protecting group.

(ii) reacting a compound of formula B

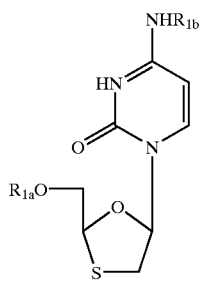

(wherein $R_{1a}$ is as defined above and $R_{1b}$ is an amino protecting group) with a fluorinating agent serving to introduce a fluorine atom in the 5-position of the cytosine ring; or (iii) reacting a compound of formula C

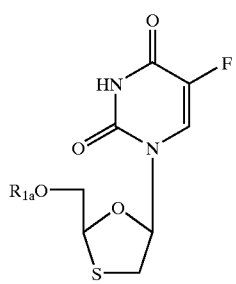

(wherein $R_{1a}$ is as defined above) with an agent serving to convert the oxo group in the 4-position of the uracil ring to an amino group; any remaining protecting groups being removed to produce the desired product.

f) a process for the preparation of a (−) or (+) enantiomer of 2-hydroxymethyl-5-(5-fluorocytosin-1-yl)-1,3-oxathiolane which comprises subjecting the compound or derivative (e.g. 5'-ester) thereof in the form of a mixture of (−) and (+) enantiomers to conditions or reacting with reagents serving to separate the enantiomers and if necessary converting the resulting derivative to the parent compound.

With regard to process e) (i), the hydroxy protecting group includes protecting groups described in detail below, including acyl (e.g. acetyl), arylacyl (e.g. benzoyl or substituted benzoyl), trityl or monomethoxytrityl, benzyl or substituted benzyl, trisubstituted silyl, including trialkylsilyl (e.g. dimethyl-t-butylsilyl) or diphenylmethylsilyl. The 5-fluorocytosine compound can be optionally protected with silyl, e.g., trisubstituted silyl groups. The protecting groups can be removed in a conventional manner. The leaving group L is a leaving group typical of those known in the art of nucleoside chemistry, e.g. halogen such as chlorine or bromine, alkoxy such as methoxy or ethoxy, or acyl such as acetyl or benzoyl.

The reaction in process e) (i) can be carried out in an organic solvent (e.g., 1,2-dichloroethane or acetonitrile) in the presence of a Lewis acid, preferably stannic chloride, or trimethylsilyl triflate.

Compounds of formula A (wherein L represents an acyl group, e.g., an acetyl group) can be obtained by reaction of a compound of formula D

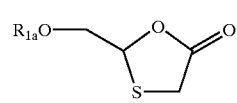

(wherein $R_1$ is defined above) with a reducing agent, e.g., a lithium aluminum hydride compound, following by treatment with the appropriate conventional reagent for the desired intermediate, for example, a carboxylic acid anhydride, e.g. acetic anhydride, for acylation, chlorinating or brominating reagents for halogenation, or alkylating reagents.

The compound of formula D can be prepared by reaction of a compound of formula E

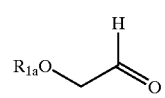

with $HSCH_2CO_2H$ at an elevated temperature.

The compound of formula E can be prepared by ozonolysis of an allyl ether or ester having the formula $CH_2=CH-CH_2-OR$ or a diether or diester of 2-butene-1,3-diol having the formula $ROCH_2-CH=CH-CH_2OR$, in which R is a protecting group, such as an alkyl, silyl, or acyl group.

With regard to process e) (ii), the 5-fluoro substituent can be introduced by methods known in the art (M. J. Robins, et al., in Nucleic Acid Chemistry, Part 2, L. B. Townsend and R. S. Tipson, editors,. J. Wiley and Sons, New York, 895–900 (19/8) and references therein; R. Duschinsky in Nucleic Acid Chemistry, Part 1, L. B. Townsend and R. S. Tipson, editors, J. Wiley and Sons, New York 43–46 (1978) and references therein). The fluorinating agent may be, for example, trimethylhypofluorite in fluorotrichloromethane.

With regard to process e) iii), the compound of formula C can be treated with 1,2,4-triazole, together with 4-chlorophenyl dichlorophosphate, to form the corresponding 4-(1,2,4-triazoylyl) compound which is then converted to the desired 4-amino (cytidine) compound by reaction with for example methanol.

The starting materials of formulas B and C can be prepared for example by reaction of an appropriate (optionally protected) base with a compound of formula A in an analogous manner to that described in process e) i). 5-Fluorouracil and 5-fluorocytosine are commercially available from Aldrich Chemical Co., Milwaukee, Wis. 53233, USA.

Resolution of the (±)-enantiomers can be accomplished as specified in detail in Section III. below.

FTC can be converted into a pharmaceutically acceptable ester by reaction with an appropriate esterifying agent, for example, an acid halide or anhydride. FTC or its pharmaceutically acceptable derivative can be converted into a pharmaceutically acceptable salt thereof in a conventional manner, for example, by treatment with an appropriate base. The ester or salt of FTC can be converted into FTC, for example, by hydrolysis.

I. Active Compound, and Physiologically Acceptable Derivatives and Salts Thereof The antivirally active compound disclosed herein is 2-hydroxymethyl-5-(5-fluorocytosin-1-yl)-1,3-oxathiolane (see FIG. 1), in the racemic form or as an isolated enantiomer.

The active compound can be administered as any derivative that upon administration to the recipient, is capable of providing directly or indirectly, the parent FTC compound, or that exhibits activity itself. Nonlimiting examples are the pharmaceutically acceptable salts (alternatively referred to as "physiologically acceptable salts"), and the 5' and $N^4$ acylated or alkylated derivatives of the active compound (alternatively referred to as "physiologically active derivatives"). In one embodiment, the acyl group is a carboxylic acid ester in which the non-carbonyl moiety of the ester group is selected from straight, branched, or cyclic alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The alkyl group can be straight, branched, or cyclic, and is optimally a $C_1$ to $C_{18}$ group.

Specific examples of pharmaceutically acceptable derivatives of FTC include, but are not limited to:

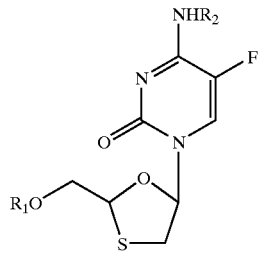

wherein $R_1$ and $R_2$ are independently selected from the group consisting of alkyl and acyl, specifically including but not limited to methyl, ethyl, propyl, butyl, pentyl, hexyl, isopropyl, isobutyl, sec-butyl, t-butyl, isopentyl, amyl, t-pentyl, 3-methylbutyryl, hydrogen succinate, 3-chlorobenzoate, cyclopentyl, cyclohexyl, benzoyl, acetyl, pivaloyl, mesylate, propionyl, butyryl, valeryl, caproic, caprylic, capric, lauric, myristic, palmitic, stearic, oleic, amino acids including but not limited to alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl, and wherein one of $R_1$ and $R_2$ can be H.

FTC or its derivatives can be provided in the form of pharmaceutically acceptable salts. As used herein, the term pharmaceutically acceptable salts or complexes refers to salts or complexes of FTC that retain the desired biological activity of the parent compound and exhibit minimal, if any, undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, and polygalacturonic acid; (b) base addition salts formed with polyvalent metal cations such as zinc, calcium, bismuth, barium, magnesium, aluminum, copper, cobalt, nickel, cadmium, sodium, potassium, and the like, or with an organic cation formed from N,N-dibenzylethylenediamine, ammonium, or ethylenediamine; or (c) combinations of (a) and (b); e.g., a zinc tannate salt or the like.

Modifications of the active compound, specifically at the $N^4$ and 5'-O positions, can affect the bioavailability and rate of metabolism of the active species, thus providing control over the delivery of the active species. Further, the modifications can affect the antiviral activity of the compound, in some cases increasing the activity over the parent compound. This can easily be assessed by preparing the derivative and testing its antiviral activity according to the methods described herein, or other method known to those skilled in the art.

II. Preparation of the Active Compounds

The racemic mixture of FTC can be prepared according to the method disclosed in detail in PCT International Publication No. WO 91/11186, published on Aug. 8, 1991, and filed by Emory University, or by the method disclosed in Example 1. In general, the method includes ozonizing either an allyl ether or ester having the formula $CH_2$=CH—$CH_2$—OR or a diether or diester of 2-butene-1,3-diol having the formula $ROCH_2$—CH=CH—$CH_2OR$, in which R is a protecting group, such as an alkyl, silyl, or acyl group, to form a glycoaldehyde having the formula OHC—$CH_2$—OR; adding thioglycolic acid to the glycoaldehyde to form a lactone of the formula 2-(R-oxy)-methyl-5-oxo-1,3-oxathiolane; reducing the lactone to various compounds containing a leaving group at the 5 position of the oxathiolane ring; coupling these compounds with silyated 5-fluorocytosine in the presence of $SnCl_4$ to form the β-isomer of FTC; and optionally removing the protecting groups.

EXAMPLE 1

Figure 2:
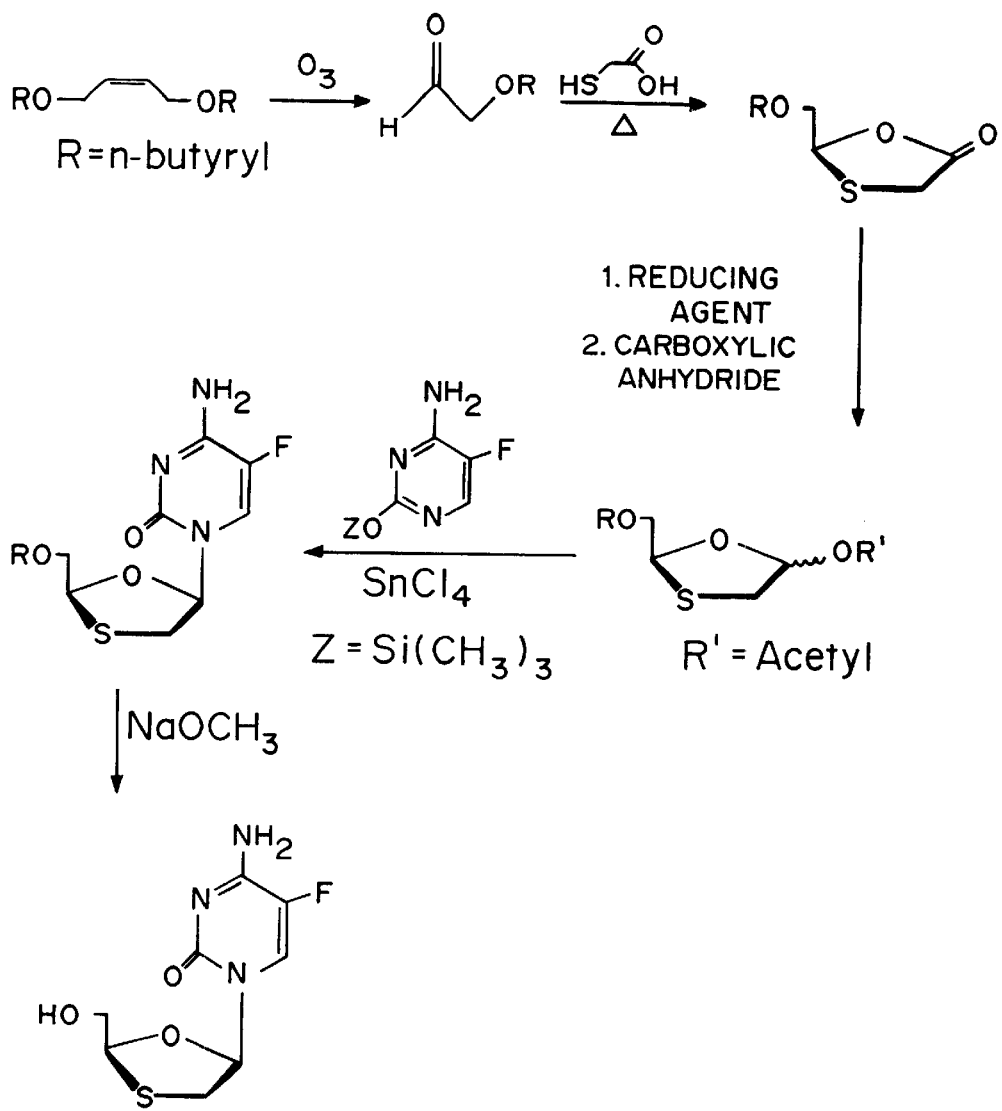
FIG. 2 is an illustration of a method for the preparation of 2-hydroxymethyl-5-(5-fluorocytosin-1-yl)-1,3-oxathiolane.

Preparation of (±)-β-D,L-2-Hydroxymethyl-5-(5-fluorocytosin-1-yl)-1, 3-oxathiolane A method for the preparation of the racemic mixture of FTC is illustrated in FIG. 2, and described in detail below. Protection of 2-Butene-1,4-diol In a dry, 2L, 3-neck flask under inert atmosphere, 100 grams (93.5 ml=1.135 mol=1.00 eq.) of 2-butene-1,4-diol and 15 grams (approx. 0.1 eq.) of DMAP (4-dimethylaminopyridine) were dissolved in 800 ml of dry pyridine and stirred while cooling to 0° C. Butyryl chloride (260 ml=2.2 eq) was then added slowly to prevent overheating and allowed to stir for one hour. The reaction was quenched with a small amount of ice water. The liquid was decanted off from the salt and evaporated in vacuo. The remaining salt was dissolved in water and the aqueous solution was extracted twice with ethyl ether. The combined other layers were washed once with saturated $CuSO_4$, twice with saturated $NaHCO_3$ containing Norit®, and then vacuum filtered through a celite® plug.

The concentrated reaction mixture was dissolved in ether and washed following the same procedure as above for the salt solution. The combined organic layers were concentrated by rotary evaporation, then placed under vacuum. This reaction is typically very close to quantitative. The scale can be easily increased as necessary. The product, 1,4-dibutyryl-2-butene-1,4-diol is a colorless to slightly yellow, clear liquid.

Ozonolysis of the Protected Diol 1,4-Dibutyryl-2-butene-1,4-diol (1.365 mol) was dissolved in 4 L of dry $CH_2Cl_2$ in a dry, 5 L 3-neck flask equipped with a large drying tube and an open tube for the introduction of gas. The tube is optimally not a fritted, gas bubbling tube that will clog on exposure to the concentrated solution. The solution was stirred and cooled to −78° C. while inert gas was bubbled through the solution. The gas inlet was sealed once the solution had cooled sufficiently, and the flask and stirring apparatus were moved to the ozone generator. Oxygen was bubbled through the stirring solution for at least 20 minutes while maintaining the ice bath. A Cryocool is ideal to maintain the low temperature for this lengthy reaction. The ozone was then introduced at 8 to 8.5 psi. Upon completion, the ozone flow was stopped, and oxygen was bubbled through the solution for about a half an hour before 3 equivalents of $Me_2S$ were added. The flask was removed from the cooling bath and transported to a hood where it was stirred for about 2 days to affect complete reduction. The solution was evaporated and put under vacuum for several hours.

This reaction typically yields approximately 95% of protected aldehyde (2-butyryloxyacetaldehyde), a colorless to yellow, clear liquid.

Cyclization of the Aldehyde With Mercaptoacetic Acid

The aldehyde (1.0 equivalent) was dissolved in toluene to provide a 0.80 to 0.85M solution in a flask equipped with a Dean Stark-type trap. Thioglycolic acid (1.1 equiv.) was added and the mixture was heated to reflux. Water was azeotropically removed via the trap. The reaction was completed in 3 hours and was allowed to cool to room temperature. The organic solution was washed twice with equal volumes of sat. $NaHCO_3$ water and once with water, dried over $MgSO_4$ and Norit, and vacuum filtered through celite before being evaporated in vacuo. The first $NaHCO_3$ wash was back extracted once with ether; the ether was washed once with water, dried over $MgSO_4$ and Norit®, vacuum filtered through celite®, and evaporated along with the other organic material from the toluene solution. The combined material was placed under vacuum overnight.

The reaction typically provides a 90% yield of 2-(butyryloxy)-methyl-5-oxo-1,3-oxathiolane.

Reduction of Lactone and Conversion to the Acetate

2-Butyryloxy-methyl-5-oxo-1,3-oxathiolane (1.00 equivalent) was dissolved in dry THF to give a 0.23M solution in a dry, 3-neck flask equipped with a mechanical stirrer and maintained under an inert atmosphere. The solution was stirred and cooled to 0° C. before 1.1 equivalent of 1.0M Li(t-BuO)$_3$AlH in THF was added via canula. The reduction was complete in approximately three hours, as indicated by TLC using 2:1 ether/hexane solvent system and an anisaldehyde stain.

Approximately 10 equivalents of freshly distilled $Ac_2O$ were then added and allowed to stir for 2 days to provide the acetylated product. The reaction was quenched by addition of saturated $NaHCO_3$, which was stirred overnight. The solution was then evaporated and stirred with more $NaHCO_3$ solution overnight. This was extracted with ether which was washed (carefully) twice with sat. $NaHCO_3$ and once with water, dried over $MgSO_4$ and Norit®, vacuum filtered through celite®, and evaporated. The product is a dark yellow, clear liquid. Gas chromatography (Init. T - 80°; Init. time=5 min.; Prog. rate - 10°/min; Final T=240° C.) typically indicates a purity of approximately 70%.

Silylation of 5-Fluorocytosine

5-Fluorocytosine (1.05 equivalents based on amount of acetylated lactol obtained in the previous step using GC indication of purity) was silylated by reflux in at least 10 equivalents of hexamethyldisilazane containing a catalytic amount of pure ammonium sulfate (0.05 to 0.10 eq.) for two hours after the solution turned clear. The flask was then sealed tightly and the solvent removed using a vacuum pump with an auxiliary trap. The product, a white solid, was left under vacuum over night until ready for use in the following coupling reaction.

Coupling of Silylated 5-Fluorocytosine With Acetylated Lactol

To silylated 5-fluorocytosine (33.86 gm. 0.124 mol) in dry dichloromethane (350 ml) was added $SnCl_4$ solution (135.6 ml, a 1 molar solution in $CH_2Cl_2$) under nitrogen atmosphere. The solution was stirred for 15 minutes at room temperature. This solution was cannulated to the solution of the lactol acetate (38 gm, 0.113 mol) in dichloromethane (400 ml) under nitrogen atmosphere over a period of 30 minutes.

The reaction solution was stirred for 2 hours, at which point the completion of reaction was indicated by TLC. The reaction solution was then diluted with dichloromethane (500 ml) and quenched with ammonium hydroxide solution. The ammonium hydroxide solution (100 ml) was added slowly maintaining the temperature of reaction below 30° C., resulting in the formation of a white precipitate.

The mixture was allowed to stir for another 30 minutes, and then passed through silica gel plug column (7 inch diameter 5 inch height). It was eluted sequentially with dichloromethane (2 L), ethyl acetate (2 L) and ethyl acetate:ethanol (9:1) (4 L). The ethyl acetate and ethyl acetate:ethanol eluents contained the desired product. These solutions were combined and evaporated at reduced pressure. The residual sticky solid was then washed with dry ether (200 ml) to give a white solid (25.35 gm; 71%), FTC-5'-butyrate.

FTC-5'-butyrate (8.74 gm; 0.026 mol) was dissolved in 250 ml methanol. Sodium methoxide (2.85 gm; 0.052 gm) was added at room temperature. The reaction was stirred for 1 hour, at which point the completion of reaction was confirmed by TLC. $NH_4Cl$ solution (10 ml) was added to quench the reaction, and then the solvent was removed under reduced pressure. The residue was absorbed on silica gel (5 gm) and passed through a small column using ethyl acetate:ethanol as an eluent (9:1). The product-containing fractions were combined and evaporated to give a sticky solid which was washed with dry ether to give white solid FTC (6.00 gm, 88%). ($^1$H NMR: (DMSO-d$^6$) 8.18 (1H, d, H$_6$, J=8.4 Hz), 7.81 & 7.57 (2H, broad, NH$_2$), 6.12 (1H, dd, H$_{1'}$, J=5.7 & 4.2 Hz), 5.40 (1H, t, OH, J=5.7 Hz), 5.17 (1H, t, 1H$_{4'}$, J=3–6 Hz), 3.74 (2H, m, 2H$_{5'}$), 3.41 (1H, dd, 1H$_{2'}$, J=5.7 & 11.7 Hz), 3.11 (1H, dd, 1H$_{2'}$, J=4.2 & 11.7 Hz); $^{13}$C NMR: (DMSO-d$^6$) 157.85 (d, J=13.4 Hz), 153.28, 136.12 (d, J=241 HZ), 126.01 (d, J=32.6 Hz), 86.90, 86.84, 62.48, 37.07; mp 195–196° C.

III. Resolution of Nucleoside Enantiomers

A method is provided herein for the resolution of racemic mixtures of nucleoside enantiomers, including but not limited to the (+) and (−) enantiomers of FTC. The method can also be used to resolve racemic mixtures of carbohydrates or carbohydrate-like moieties, such as derivatives of 1,3-oxathiolane and 1,3-dioxolane. The method involves the use of an enzyme that preferentially catalyzes a reaction of one enantiomer in a racemic mixture. The reacted enantiomer is separated from the unreacted enantiomer on the basis of the new difference in physical structure. Given the disclosure herein, one of skill in the art will be able to choose an enzyme that is selective for the nucleoside enantiomer of choice (or selective for the undesired enantiomer, as a method of eliminating it), by selecting one of the enzymes discussed below or by systematic evaluation of other known enzymes. Given this disclosure, one of skill in the art will also know how to modify the substrate as necessary to attain the desired resolution. Through the use of either chiral NMR shift reagents, polarimetry, or chiral HPLC, the optical enrichment of the recovered ester can be determined.

The following examples further illustrate the use of enzymes to resolve racemic mixtures of enantiomers. Other known methods of resolution of racemic mixtures can be used in combination with the method of resolution disclosed herein. All of these modifications are considered within the scope of the invention.

Resolution Based on Hydrolysis of C5'-Nucleoside Esters

In one embodiment, the method includes reacting the C5'-hydroxyl group of a mixture of nucleoside racemates with an acyl compound to form C5'-esters in which the nucleoside is in the "carbinol" end of the ester. The racemic mixture of nucleoside C5'-esters is then treated with an enzyme that preferentially cleaves, or hydrolyses, one of the enantiomers and not the other, in a given time period.

An advantage of this method is that it can be used to resolve a wide variety of nucleosides, including pyrimidine and purine nucleosides that are optionally substituted in the carbohydrate moiety or base moiety. The method can also be used to resolve nucleoside derivatives that contain additional heteroatoms in the carbohydrate moiety, for example, FTC and BCH-189. The broad applicability of this method resides in part on the fact that although the carbinol portion of the ester plays a role in the ability of an enzyme to differentiate enantiomers, the major recognition site for these enzymes is in the carboxylic acid portion of the ester. Further, one may be able to successfully extrapolate the results of one enzyme/substrate study to another, seemingly-different system, provided that the carboxylic acid portions of the two substrates are the same or substantially similar.

Another advantage of this method is that it is regioselective. Enzymes that hydrolyse esters typically do not catalyze extraneous reactions in other portions of the molecule. For example, the enzyme lipase catalyses the hydrolysis of the ester of 2-hydroxymethyl-5-oxo-1,3-oxathiolane without hydrolysing the internal lactone. This contrasts markedly with "chemical" approaches to ester hydrolysis.

Still another advantage of this method is that the separation of the unhydrolysed enantiomer and the hydrolysed enantiomer from the reaction mixture is quite simple. The unhydrolysed enantiomer is more lipophilic than the hydrolysed enantiomer and can be efficiently recovered by simple extraction with one of a wide variety of nonpolar organic solvents or solvent mixtures, including hexane and hexane/ether. The less lipophilic, more polar hydrolysed enantiomer can then be obtained by extraction with a more polar organic solvent, for example, ethyl acetate, or by lyophilization, followed by extraction with ethanol or methanol. Alcohol should be avoided during the hydrolysis because it can denature enzymes under certain conditions.

Enzymes and Substrates

With the proper matching of enzyme and substrate, conditions can be established for the isolation of either nucleoside enantiomer. The desired enantiomer can be isolated by treatment of the racemic mixture with an enzyme that hydrolyses the desired enantiomer (followed by extraction of the polar hydrolysate with a polar solvent) or by treatment with an enzyme that hydrolyses the undesired enantiomer (followed by removal of the undesired enantiomer with a nonpolar solvent).

Enzymes that catalyze the hydrolysis of esters include esterases, for example pig liver esterase, lipases, including porcine pancreatic lipase and Amano PS-800 lipase, substillisin, and α-chymotrypsin.

Figure 3:
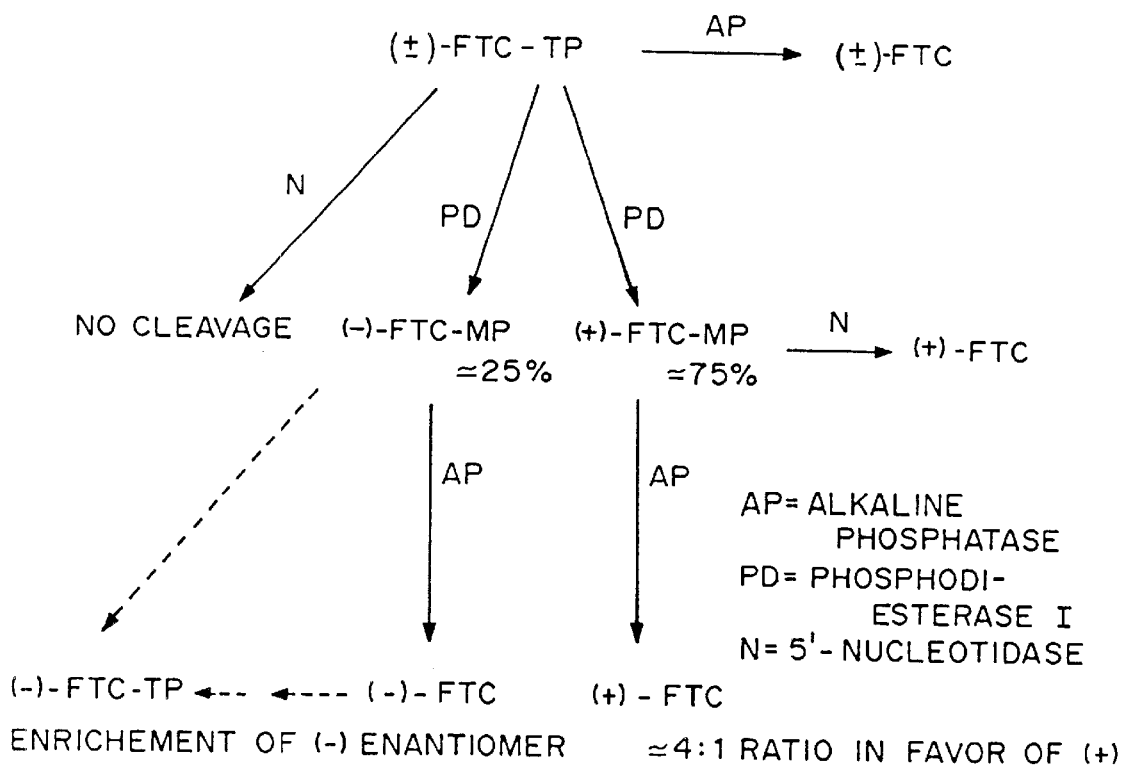
FIG. 3 is a flow chart of the specificity of alkaline phosphatase and snake venom phosphodiesterase for the (+) and (−) enantiomers of FTC.

FIG. 3 is a flow chart of the specificity of alkaline phosphatase and snake venom phosphodiesterase for the (+) and (−) enantiomers of FTC. As indicated, alkaline phosphatase hydrolyses the triphosphate of both of the enantiomers to FTC, and therefore is not effective as a separation means. Phosphodiesterase I preferentially hydrolyses the (+)-isomer of FTC to its monoester, which can then be exposed to 5'-nucleotidase to provide (+)-FTC.

The most effective acyl group to be used to esterify the C5'-position of the nucleoside can be determined without undue experimentation by evaluation of a number of homologs using the selected enzyme system. For example, when 1, 3-oxathiolane nucleosides are esterified with butyric acid, resolutions with both pig liver esterase and Amano PS-800 proceed with high enantioselectivity (94–100% enantiomeric excess) and opposite selectivity. Pig liver esterase preferentially hydrolyses the (+)-enantiomer of FTC, and Amano PS-800® preferentially hydrolyses the (−)-enantiomer of FTC. The percent enantiomeric excess reported in Table 1 is the amount of purified butyrate ester remaining in the enzyme treated mixture (i.e., the butyrate ester of (−)-FTC in the case of PLE and the butyrate ester of (+)-FTC in the case of Amano PS-800®).

Non-limiting examples of acyl groups that can be evaluated for use with a particular nucleoside enantiomeric mixture and particular enzyme include alkyl carboxylic acids and substituted alkyl carboxylic acids, including acetic acid, propionic acid, butyric acid, and pentanoic acid. With certain enzymes, it may be preferred to use an acyl compound that is significantly electron-withdrawing to facilitate hydrolysis by weakening the ester bond. Examples of electron-withdrawing acyl groups include α-haloesters such as 2-chloropropionic acid, 2-chlorobutyric acid, and 2-chloropentanoic acid. α-Haloesters are excellent substrates for lipases.

Resolution Conditions

The enzymatic hydrolyses are typically carried out with a catalytic amount of the enzyme in an aqueous buffer that has a pH that is close to the optimum pH for the enzyme in question. As the reaction proceeds, the pH drops as a result of liberated carboxylic acid. Aqueous base should be added to maintain the pH near the optimum value for the enzyme.

The progress of the reaction can be easily determined by monitoring the change in pH and the amount of base needed to maintain pH. The hydrophobic ester (the unhydrolysed enantiomer) and the more polar alcohol (the hydrolysed enantiomer) can be sequentially and selectively extracted from the solution by the judicious choice of organic solvents. Alternatively, the material to be resolved can be passed through a column that contains the enzyme immobilized on a solid support.

Enzymatic hydrolyses performed under heterogeneous conditions can suffer from poor reproducibility. Therefore, it is preferred that the hydrolysis be performed under homogeneous conditions. Alcohol solvents are not preferred because they can denature the enzymes. Homogeneity can be achieved through the use of non-ionic surfactants, such as Triton X-100. However, addition of these surfactants not only assists in dissolving the starting material, they also enhance the aqueous solubility of the product. Therefore, although the enzymatic reaction can proceed more effectively with the addition of a non-ionic surfactant than under heterogeneous conditions, the isolation of both the recovered starting material and the product can be made more difficult. The product can be isolated with appropriate chromatographic and chemical (e.g., selective salt formation) techniques. Diacylated nucleosides can be used but are often quite lipophilic and hard to dissolve in the medium used.

EXAMPLE 2

Enantioselective Lipase-Catalyzed Hydrolysis of FTC Esters

A number of 5'-O-acyl derivatives of FTC were prepared by selective O-acylation of the N-hydrochloride salt (see Table 1 and FIG. 4) of (±)-FTC. The efficiency of the hydrolysis of the derivatives by lipases was investigated. As shown in Table 1, pig liver esterase (PLE) exhibits a high level of selectivity for the hydrolysis of the ester of the (+)-enantiomer of FTC, leaving predominately the butyrate of (−)-FTC in the HPLC-analyzed mixture. In contrast, PS-800 hydrolyses the ester of the (−)-enantiomer of FTC preferentially, leaving predominately the butyrate of the (+)-FTC in the HPLC-analyzed mixture. The rate of the hydrolysis was also found to be dependent on the nature of the acyl group; the acetyl derivative was significantly slower than the butyryl derivative. It has now been discovered that the rate of the hydrolysis of the propionic acid ester of FTC is even faster than that observed for the butyrate derivative. Percent recovery and percent of enantiomeric excess were both determined using HPLC. Although the enantioselectivity is excellent when employing PLE (typically 97% e.e. or higher), additional enrichment can be accomplished by sequential enzymatic hydrolysis reactions in which the enantiomerically-enriched butyrate from a PLE-catalyzed hydrolysis is subjected to enzymatic hydrolysis by PS-800.

TABLE 1

Comparison of Effect of Ester on Enzyme Hydrolysis

| Substrate | % Recovery | % E.E. (s.m.) |
|---|---|---|
| FTC Esters with PLE: | | (−) −FTC |
| | | (butyrate) |
| acetate | 32.68 | N.D. |
| propionate | 39.87 | N.D. |

TABLE 1-continued

Comparison of Effect of Ester on Enzyme Hydrolysis

| Substrate | % Recovery | % E.E. (s.m.) |
|---|---|---|
| butyrate | 48.00 | 98 |
| butyrate | 45.71 | 98.6 |
| FTC Esters with PS800: | | (+) −FTC |
| | | butyrate |
| acetate | 73.17 | N.D. |
| propionate | 52.67 | N.D. |
| butyrate | 58.34 | N.D. |
| valerate | 41.50 | 94 |

EXAMPLE 3

Figure 4:
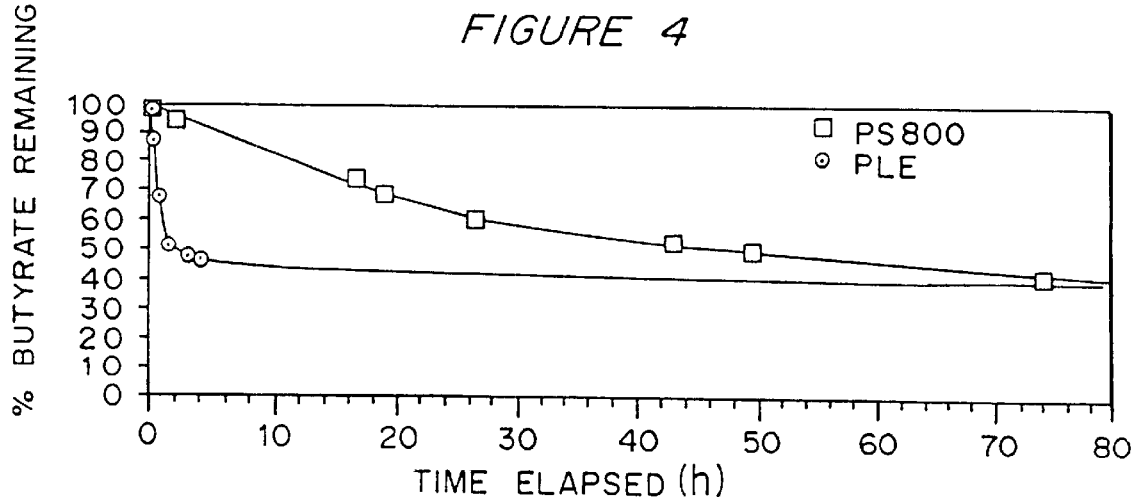
FIG. 4 is a graph indicating the progress of lipase-catalyzed hydrolysis of the 5'-butyryl ester of FTC over time using the enzymes Amano PS-800® (-open square-) and PLE (-open circle with dot-).

Procedure for the Preparation of (+)- and (−)-FTC via Enantioselective, Lipase-Catalyzed Hydrolysis of FTC Butyrate The 5'-O-butyrate of (±)-FTC (0.47 mmol, 149 mg) was dissolved in 16 mL of a solution of 4:1 pH 8 buffer:$CH_3CN$. The clear solution was stirred and treated with 26 mg of pig liver esterase (PLE-A). The progress of the reaction was monitored by HPLC (FIG. 4). After 20 hours (52% conversion), the reaction mixture was extracted with 2×80 mL of $CHCl_3$ and 80 mL of ethyl acetate. The organic layer extracts were combined, dried over anhydrous $MgSO_4$, filtered, and concentrated by rotary evaporation. The resulting residue was eluted on 2×1000 m pTLC plates using ethyl acetate as eluant (double elution) to give, after isolation, 53 mg (36% based on starting material) of FTC butyrate which was determined to have 98% enantiomeric excess (e.e.) by HPLC analysis. The enantiomerically-enriched butyrate was then treated with 1.6 mL of methanol followed by 0.38 mmol (20 mg) of sodium methoxide. The resulting mixture was stirred at room temperature, and the progress of the reaction was monitored by HPLC. The reaction was completed within 30 minutes. The solvent was removed by rotary evaporation to give a crude white solid (76 mg) that was eluted on a 1000 m PTLC using 5:1 ethyl acetate:ethanol. (−)-FTC was isolated as a white solid (33 mg; 82% yield). HPLC analysis of the FTC as its 5'-O-acetate derivative showed 97% e.e.; $[\alpha](^{20}{}_{,D})$ −120.5° (c=0.88; abs. ethanol).

Emulsions in the work-up step can be avoided by adding $HCCl_3$ to the reaction mixture on completion (which also serves to denature the enzyme), stripping the solvents under vacuum, and then extracting with $HCCl_3$.

Similarly, 1.2 mmol (375 mg) of the 5'-O-butyrate of (±)-FTC was dissolved in 40 mL of 4:1 pH 8 buffer-$CH_3CN$. The clear solution was stirred and treated with 58 mg of pig liver esterase (PLE-A). The progress of the reaction was monitored by HPLC. After 90 minutes (38% conversion), the reaction mixture was added to 150 mL of $CHCl_3$. The layers were separated and the aqueous layer lyophilized to remove solvent. The white residue from the lyophilization was extracted with 3×10 mL of absolute ethanol. The extracts were filtered, combined, and concentrated in vacuo to yield 179 mg of crude oil. The crude material was eluted on a 45×30 mm column of silica gel using 3×75 mL of ethyl acetate followed by 5:1 ethyl acetate-ethanol. (+)-FTC was isolated as a white solid (109 mg; 37% based on starting butyrate). HPLC analysis of the (+)-FTC as its 5'-O-acetate derivative showed 97.4% e.e.; $[a]O(^{20}{}_{,D})$ +113.4° (c=2.53; absolute ethanol)

A similar reaction was performed using 0.12 mmol (37 mg) of the 5'-O-butyrate of FTC and 7 mg of PS-800 in 4.0 mL of 4:1 pH 8 buffer:CH$_3$CN. The reaction was considerably slower than that with PLE-A and required 74 hours for 59% conversion. The recovered butyrate (11.4 mg; 31% of the initial amount) was found to exhibit 94% e.e. by HPLC.

Resolution of Nucleoside Enantiomers With Cytidine-Deoxycytidine Deaminase

In an alternative embodiment, cytidine-deoxycytidine deaminase is used to resolve racemic mixtures of 2-hydroxymethyl-5-(cytosin-1-yl)-1,3-oxathiolane and its derivatives, including 2-hydroxymethyl-5-(5-fluorocytosin-1-yl)-1, 3-oxathiolane. The enzyme catalyses the deamination of the cytosine moiety to a uracil. It has been discovered that one of the enantiomers of 1,3-oxathiolane nucleosides is a preferred substrate for cytidine-deoxycytidine deaminase. The enantiomer that is not converted to a uracil derivative (and therefore is still basic) is extracted from the solution with an acidic solution. Care should be taken to avoid strong acidic solutions (pH below 3.0), that may cleave the oxathiolane ring.

Cytidine-deoxycytidine deaminase can be isolated from rat liver or human liver, or expressed from recombinant sequences in a procaryotic system such as in *E. coli*.

The method of resolution of cytidine nucleoside enantiomers using cytidine-deoxycytidine deaminase can be used as the sole method of resolution or can be used in combination with other methods of resolution, including resolution by enzymatic hydrolysis of 5'-O-nucleoside esters as described above.

Combination of Enzymatic Resolution With Classical Resolution Methods

The process described above for resolving racemic mixtures of nucleoside enantiomers can be combined with other classical methods of enantiomeric resolution to increase the optical purity of the final product.

Classical methods of resolution include a variety of physical and chemical techniques. Often the simplest and most efficient technique is recrystallization, based on the principle that racemates are often more soluble than the corresponding individual enantiomers. Recrystallization can be performed at any stage, including on the acylated compounds or the final enantiomeric product. If successful, this simple approach represents a method of choice.

When recrystallization fails to provide material of acceptable optical purity, other methods can be evaluated. If the nucleoside is basic (for example, a cytidine) one can use chiral acids that form diastereomeric mixtures that may possess significantly different solubility properties. Nonlimiting examples of chiral acids include malic acid, mandelic acid, dibenzoyl tartaric acid, 3-bromocamphor-8-sulfonic acid, 10-camphorsulfonic acid, and di-p-toluoyltartaric acid. Similarly, acylation of the free hydroxyl group with a chiral acid derivative also results in the formation of diastereomeric mixtures whose physical properties may differ sufficiently to permit separation.

Small amounts of enantiomerically enriched nucleosides can be obtained or purified by passing the racemic mixture through an HPLC column that has been designed for chiral separations, including cyclodextrin bonded columns marketed by Rainin Corporation.

EXAMPLE 4

Separation of Racemic Mixtures of Nucleosides by HPLC

The resolutions of the C4'-enantiomers of (±)-FTC were performed using a chiral cyclodextrin bonded (cyclobond AC-I) column obtained from Rainin Corporation (Woburn, Mass.). The conditions were as follows: Isocratic 0.5% methanol in water; flow rate 1 ml/min., UV detection at 262 nm. HPLC grade methanol was obtained from J. T. Baker (Phillipsburg, N.J.). The racemic mixtures were injected and fractions were collected. Fractions containing each of the enantiomers were pooled, frozen, and then lyophilized. The compounds were characterized by UV spectroscopy and by their retention times on HPLC. In general, the (−)-enantiomers have lower retention times than the (+)-enantiomers (see *J. Liouid Chromatography* 7:353–376, 1984). The concentrations of the compounds were determined by UV spectroscopy, using a stock solution of known concentration (15 μM) prepared in water for biological evaluation. The retention times for the separated enantiomers are provided in Table 2.

TABLE 2

Retention Times of Enantiomers of FTC

| Compound | R$_f$ (min) |
|---|---|
| (−)−FTC | 8.3 |
| (+)−FTC | 8.7 |

EXAMPLE 5

Alternative Methods for Separating FTC Enantiomers Using a Chiral Column

Using a Cyclobond I-Ac column (5 μm, 25 cm×4.6 mm, Rainin Corporation, Woburn, Mass., catalog no. AST-41049), with a flow rate of 0.6 ml/min of 0.5% isocratic methanol (Fisher Scientific, Inc. HPLC grade, cat no. A-452-4 in water), and UV detection at 262 nm, the FTC enantiomers exhibited retention times of 12.68 minutes ((−)-FTC) and 13.20 minutes ((+)-FTC).

Using a Chiralpak AS column (10 μm, 25 cm×4.6 mm, J. T. Baker Inc., Phillisburg, N.J., catalog no. 7406-00, serial no. 09-29-10320) with a flow rate of 0.8 ml/min of isopropyl alcohol (HPLC grade, Fisher Scientific, Inc., cat no. A-451-4) and UV detection of 262 nm, the FTC enantiomers exhibited retention times of 5.9 minutes ((−)-FTC), and 9.8 minutes ((+)-FTC)

IV. Ability of 2-Hydroxymethyl-5-(5-fluorocytosin-1-yl)-1, 3-oxathiolane ("FTC") to Inhibit the Replication of HIV It is often desirable to screen a number of racemic mixtures of nucleosides as a preliminary step to determine which warrant further resolution into enantiomerically enriched components and further evaluation of antiviral activity. The ability of nucleosides to inhibit HIV can be measured by various experimental techniques. The technique used herein, and described in detail below, measures the inhibition of viral replication in phytohemagglutinin (PHA) stimulated human peripheral blood mononuclear (PBM) cells infected with HIV-1 (strain LAV). The amount of virus produced is determined by measuring the virus-coded reverse transcriptase enzyme. The amount of enzyme produced is proportional to the amount of virus produced. Table 3 provides the EC$_{50}$ values (concentration of nucleo side that inhibits the replication of the virus by 50% in PBM cells, estimated 10% error factor) and $IC_{50}$ values (concentration of nucleoside that inhibits 50% of the growth of mitogen-stimulated uninfected human PBM cells) of a number of (±)-1,3-oxathiolane and nucleosides.

EXAMPLE 6

Anti-HIV Activity of (±)-1,3-Oxathiolans Nucleosides

A. Three-day-old phytohemagglutinin-stimulated PBM cells ($10^6$ cells/ml) from hepatitis B and HIV-1 seronegative healthy donors were infected with HIV-1 (strain LAV) at a concentration of about 100 times the 50% tissue culture infectious dose (TICD 50) per ml and cultured in the presence and absence of various concentrations of antiviral compounds.

B. Approximately one hour after infection, the medium, with the compound to be tested (2 times the final concentration in medium) or without compound, was added to the flasks (5 ml; final volume 10 ml). AZT was used as a positive control.

C. The cells were exposed to the virus (about $2 \times 10^5$ dpm/ml, as determined by reverse transcriptase assay) and then placed in a $CO_2$ incubator. HIV-1 (strain LAV) was obtained from the Center for Disease Control, Atlanta, Ga. The methods used for culturing the PBM cells, harvesting the virus and determining the reverse transcriptase activity were those described by McDougal et al. (*J. Immun. Meth.* 76, 171–183, 1985) and Spira et al. (*J. Clin. Meth.* 25, 97–99, 1987), except that fungizone was not included in the medium (see Schinazi, et al., *Antimicrob. Agents Chemother.* 32, 1784–1787 (1988); Id., 34:1061–1067 (1990)).

D. On day 6, the cells and supernatant were transferred to a 15 ml tube and centrifuged at about 900 g for 10 minutes. Five ml of supernatant were removed and the virus was concentrated by centrifugation at 40,000 rpm for 30 minutes (Beckman 70.1 Ti rotor). The solubilized virus pellet was processed for determination of the levels of reverse transcriptase. Results are expressed in dpm/ml of sampled supernatant. Virus from smaller volumes of supernatant (1 ml) can also be concentrated by centrifugation prior to solubilization and determination of reverse transcriptase levels.

The median effective ($EC_{50}$) concentration was determined by the median effect method (*Antimicrob. Agents Chemother.* 30, 491–498 (1986). Briefly, the percent inhibition of virus, as determined from measurements of reverse transcriptase, is plotted versus the micromolar concentration of compound. The $EC_{50}$ is the concentration of compound at which there is a 50% inhibition of viral growth.

E. Mitogen stimulated uninfected human PBM cells ($3.8 \times 10^5$ cells/ml) were cultured in the presence and absence of drug under similar conditions as those used for the antiviral assay described above. The cells were counted after 6 days using a hemacytometer and the trypan blue exclusion method, as described by Schinazi et al., *Antimicrobial Agents and Chemotherapy*, 22(3), 499 (1982). The $IC_{50}$ is the concentration of compound which inhibits 50% of normal cell growth.

TABLE 3

$EC_{50}$ and $IC_{50}$ of Various Analogues of 1,3-Oxathiolane Nucleosides in Human PBM Cells

| Code | X or Y | R | Antiviral $EC_{50}$, μM | Cytotoxicity $IC_{50}$, μM |
|---|---|---|---|---|
| DLS-009 | X = O | H | >100 | >100 |
| DLS-010 | X = O | Me | 64.4 | >100 |
| DLS-027 | X = O | F | >100 | >100 |
| DLS-028 | X = O | Cl | 60.8 | >100 |
| DLS-044 | X = O | Br | >100 | >100 |
| DLS-029 | X = O | I | >100 | >100 |
| DLS-020 | Y = $NH_2$ | H | 0.02 | >100 |
| DLS-011 | Y = $NH_2$ | Me | >10 | >100 |
| DLS-022 | Y = $NH_2$ | F | 0.01 | >100 |
| DLS-023 | Y = $NH_2$ | Cl | 38.7 | >100 |
| DLS-021 | Y = $NH_2$ | Br | 77.4 | >100 |
| DLS-026 | Y = $NH_2$ | I | 0.72 | >100 |
| DLS-058(−) | Y = $NH_2$ | F | 0.008 | >100 |
| DLS-059(+) | Y = $NH_2$ | F | 0.84 | >100 |
| DLS-053 | Y = $NH_2$ | $CF_3$ | 60.7 | >100 |

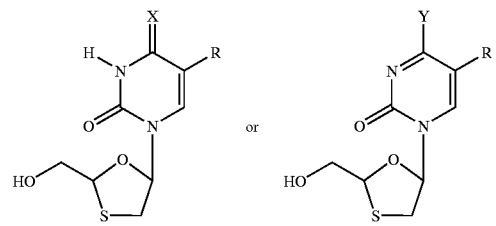

As indicated in Table 3, in general, the substituted cytosine 1,3-oxathiolane nucleosides are more active than the corresponding uracil nucleosides. The error in $EC_{50}$ and $IC_{50}$ measurements are estimated at ±10%.

One of the compounds, (±)-FTC, (referred to as "DLS-022", compound 8) not only exhibits exceptional activity (approximately 10 nM in PBM cells), but also quite low toxicity (>100 μM in PBM, Vero and CEM cells). Further, the (−)-enantiomer of FTC (DLS-058), exhibits significantly greater activity than the racemic mixture.

The $IC_{50}$ of (±)-FTC was over 100 μM, indicating that the compound was not toxic in uninfected PBM cells evaluated up to 100 μM.

EXAMPLE 7

Antiviral Activity of the Enantiomers of FTC Resolved by UPLC

Figure 5:
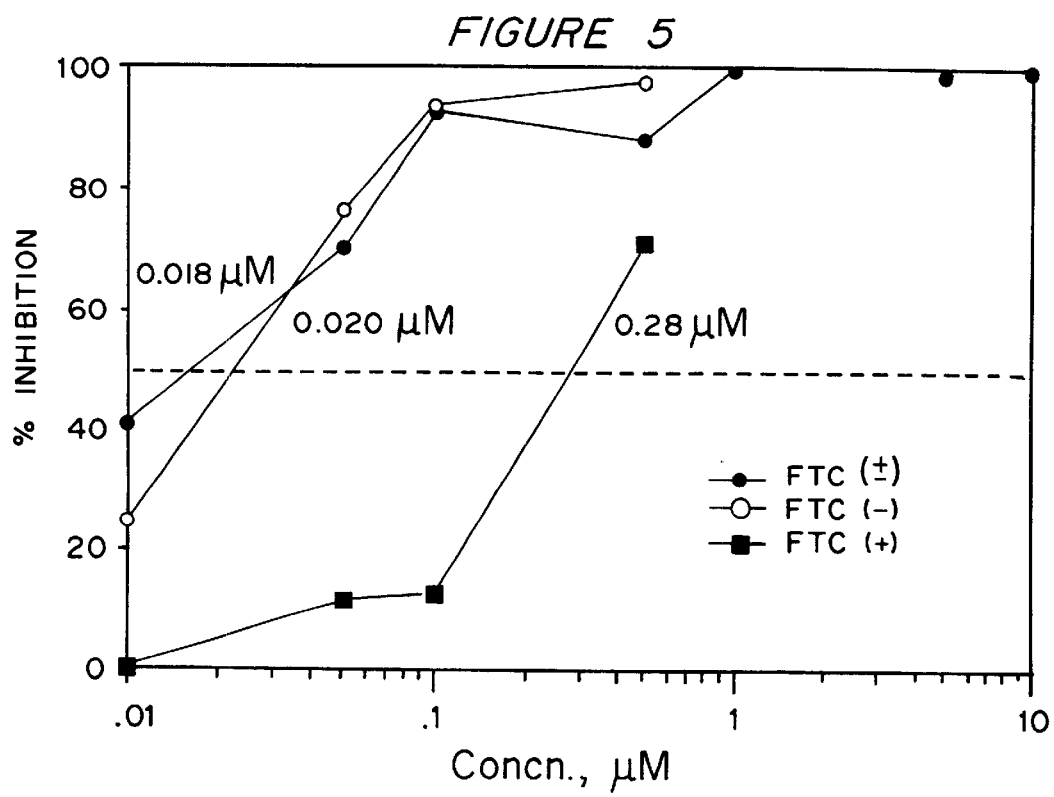
FIG. 5 is a graph of the effect of concentration ($\mu$M) of racemic and enantiomerically enriched FTC (prepared by the method of Example 4) versus the percent inhibition of human PBM cells infected with HIV-1. ((-darkened circle-, (±)-FTC), (-open circle-,(−)-FTC), (-darkened square-, (+)-FTC).

The enantiomers of FTC were isolated by the method of Example 4, and the antiviral activity evaluated by the method of Example 6. The results are provided in Table 4, and illustrated in FIG. 5.

TABLE 4

Antiviral Activity of the (+) and (−) Enantiomers of FTC

| Treatment Concn., μM | | DPM/ml | % Inhibition (Corrected) | $EC_{50}$: μM |
|---|---|---|---|---|
| FTC (±) | 0.0001 | 73,755 | 26.6 | 0.018 |
| | 0.005 | 83,005 | 16.3 | |
| | 0.01 | 60,465 | 41.3 | |
| | 0.05 | 34,120 | 70.4 | |
| | 0.1 | 14,160 | 92.4 | |
| | 0.5 | 18,095 | 88.1 | |
| | 1 | 7,555 | 99.7 | |
| | 5 | 7,940 | 99.3 | |
| | 10 | 5,810 | 101.7 | |
| FTC (−) | 0.001 | 76,275 | 23.8 | 0.02 |

TABLE 4-continued

Antiviral Activity of the (+) and (−) Enantiomers of FTC

| Treatment Concn., μM | | DPM/ml | % Inhibition (Corrected) | EC$_{50}$: μM |
|---|---|---|---|---|
| | 0.005 | 58,590 | 43.3 | |
| | 0.01 | 75,350 | 24.8 | |
| | 0.05 | 28,890 | 76.2 | |
| | 0.1 | 13,175 | 93.5 | |
| | 0.5 | 9,485 | 97.6 | |
| FTC (+) | 0.001 | 94,340 | 3.8 | 0.28 |
| | 0.005 | 107,430 | −10.6 | |
| | 0.01 | 99,465 | −1.8 | |
| | 0.05 | 87,120 | 11.8 | |
| | 0.1 | 86,340 | 12.7 | |
| | 0.5 | 33,225 | 71.4 | |

As indicated in Table 4, in this experiment the (−)-enantiomer of FTC appears to be approximately one order of magnitude more potent than the (+)-FTC enantiomer, and has approximately the same anti-HIV activity as the racemic mixture. Neither the enantiomers nor the racemic mixture is toxic up to 100 μM as measured by the Trypan Blue exclusion method in human PBM cells.

EXAMPLE 8

Antiviral Activity of FTC Enantiomers Resolved by Method of Example 3

Figure 6:
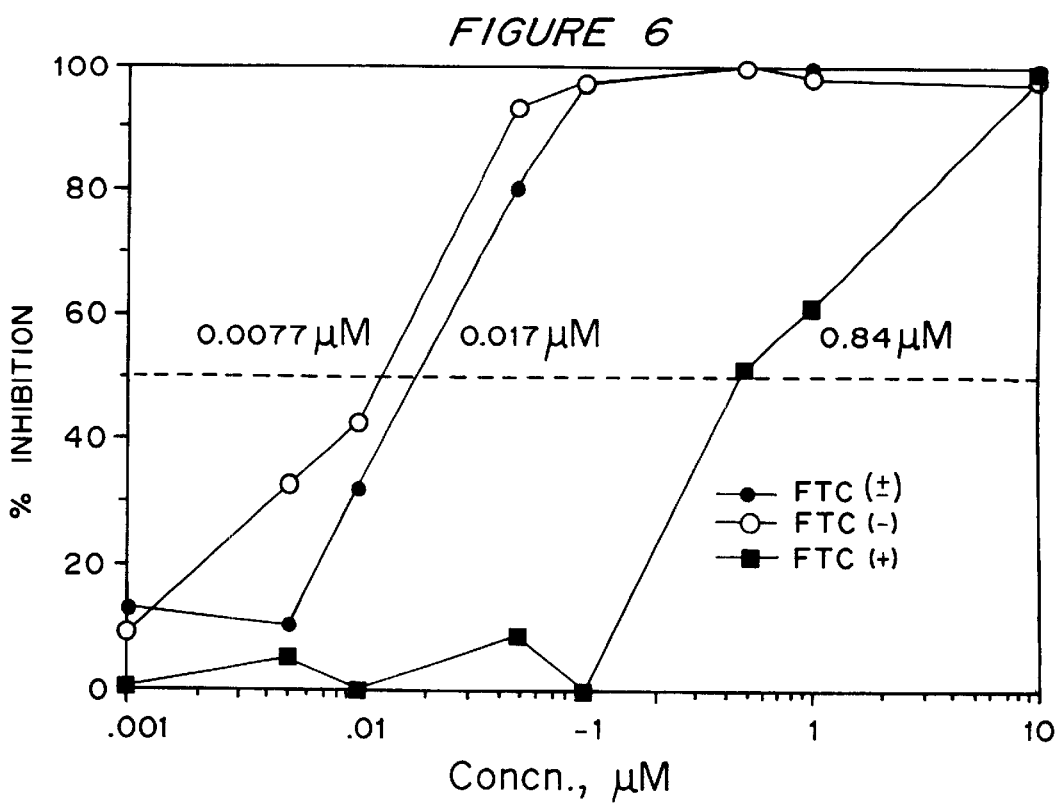
FIG. 6 is a graph of the effect of concentration ($\mu$M) of racemic and enantiomerically enriched FTC (prepared by method of Example 3) on the percent inhibition of human PBM cells infected with HIV-1. ((-darkened circle-, (±)-FTC), (-open circle-,(−)-FTC), (-darkened square-, (+)-FTC).

The enantiomers of (±)-FTC were also resolved by the method of Example 3, and the antiviral activity evaluated by the method of Example 6. The results are illustrated in FIG. 6. As indicated in FIG. 6, the EC$_{50}$ of the racemic mixture of FTC was 0.017 μM, the EC$_{50}$ of (−)-FTC at 0.0077 4μM, and the EC$_{50}$ of (+)-FTC at 0.84 μM.

EXAMPLE 9

Uptake of (±)-FTC Into Human PBX Cells

Studies were undertaken using radiolabeled FTC to follow the intracellular profiles of the parent drug and metabolites detected within the cell. All studies were conducted in duplicate. Human peripheral blood mononuclear cells (PBM cells) were suspended in RPMI 1640 medium containing 10% fetal calf serum and antibiotics (2×10$^6$ cells/ml), 10 ml per timepoint) and incubated with addition of 10 μM FTC (specific activity about 700 dpm/pmol). Cells were exposed to the drug for 2, 6, 12, and 24 hours. At these timepoints, the medium was removed and the cells were washed two times with cold Hank's balanced salt solution. Extraction was performed with addition of 0.2 ml of 60% cold methanol/water and stored overnight at −70° C. The following morning, the suspensions were centrifuged and extractions were repeated two times for 0.5 hours at −700° C. The total supernatants (0.6 ml) were lyophilized to dryness. The residues were resuspended in 250 μl of water and aliquots of between 50 and 100 μl were analyzed by HPLC. Quantitation of intracellular parent drug and metabolic derivatives were conducted by HPLC. Because of the potential acid lability of some compounds, a buffer system close to physiological pH was used for the separation of the metabolites.

Figure 7:
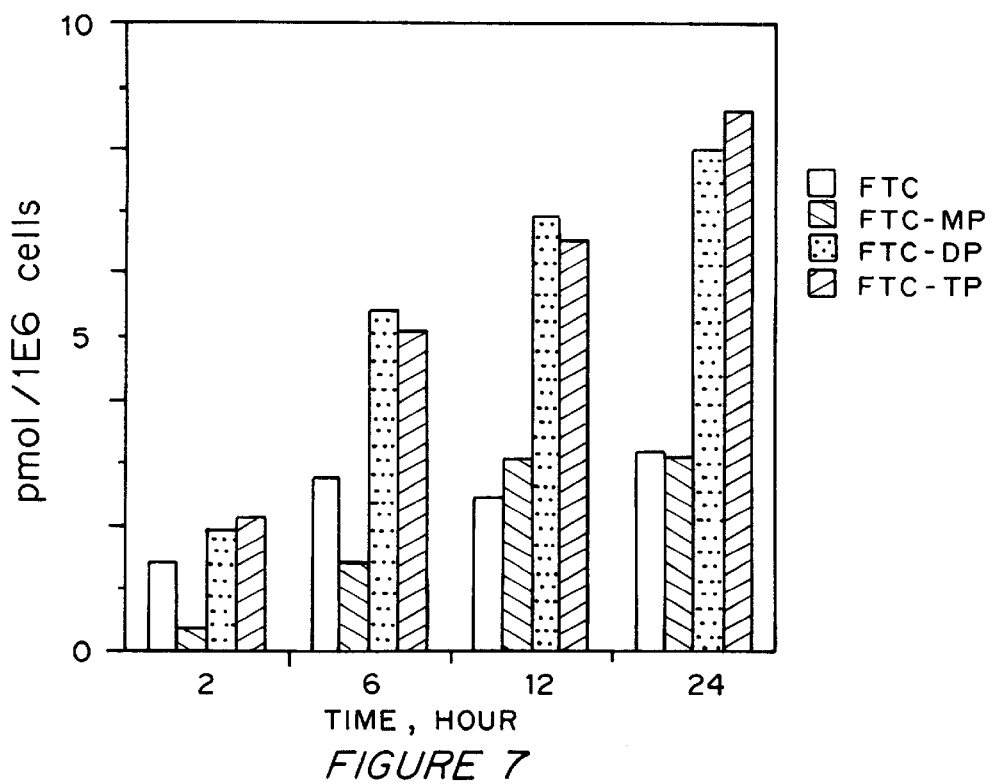
FIG. 7 is a graph of the uptake of tritiated (±)-FTC in human PBM cells (average of two determinations) in time (hours) versus pmol/$10^6$ cells.

FIG. 7 is a graph of the presence (uptake) of tritiated (±)-FTC in human PBM cells (average of two determinations) in time (hours) versus pmol/10$^6$ cells. The uptake studies indicate that radiolabeled FTC is readily taken up in human lymphocytes, that produce very large amounts of the 5'-triphosphate derivative of FTC.

EXAMPLE 10

Antiretroviral Activity of PTC in Various Cell Lines

The antiretroviral activity of FTC was measured in a number of cell lines using procedures similar, but not identical, to that set out in Example 6. Cell lines were obtained from either human donors, AIDS Research and Reference Reagent Program, NIH, Rockville, Md., ATCC, or the Red Cross. The CEM thymidine kinase deficient cells were prepared by sequential passage of CEM cells in the presence of 5-bromo-2'-deoxyuridine. The results are provided in Table 5.

TABLE 5

Antiretroviral Activity cf FTC In Different Cell Systems

| Cell system (Virus strain) | EC$_{50}$ (μM) (+) −FTC |
|---|---|
| HIV-1 | |
| PBMC (LAV-1) | 0.027 |
| MT2 (HTLV$_{IIIB}$) | 0.89 |
| CEM (LAV-1) | 0.08 |
| CEM-TK$^{(−)}$ (LAV-1) | 0.026 |
| CEM (HTLV$_{IIIB}$) NIH | 0.09 |
| HIV-2 | |
| PBMC (ROD2) | 0.0038 (±) −FTC |
| | 0.0007 (−) −FTC |
| | 0.026 (+) −FTC |
| SIV | |
| AA-2 (SIV251) | 4.6 |
| C-8166 (SIV251) | <8.0 |
| FIV | |
| CrFK (61E) | ≤1 |

EXAMPLE 11

Egress of (±)-FTC, from Human PBM Cells

Studies were performed using radiolabeled FTC to follow the intracellular profiles of the parent drug and metabolites detected within the cell after incubation in media with drug for 24 hours, and then removal of drug. This study measures the time needed for intracellular levels of triphosphates to decline. Studies were conducted in duplicate. Uninfected cells (2×10$^6$ ml) were suspended in the appropriate medium supplemented with serum (10 ml per timepoint) and incubated at 37° C. in a 5% CO$_2$ incubator. The radiolabeled FTC concentration was 10 μM. After pulsing the cells with the labeled compound for 24 hours, the cells were thoroughly washed and then replenished with fresh medium without the antiviral drugs (0 hr). At 0, 2, 4, 6, 12, 24, and 48 hours (second incubation time), the cells were removed, and immediately extracted with 60% cold methanol/water. The extract was obtained by centrifugation and removal of the cell pellet. The extracts were lyophilized and then stored at −70° C. Prior to analysis, the material was resuspended in 250 microliters of HPLC buffer and immediately analyzed. Quantitation of intracellular parent drug and metabolic derivatives was conducted by HPLC, using either a Micromeritics or Hewlett-Packard model 1090 PHLC system with an anion exchange Partisil 10 SAX column (Whatman, Inc.), at a flow rate of 1 ml/min, 1 kpsi pressure, with UV detection at 262 nm. The mobile phase consisted of deionized water (A), 2 mM NaH$_2$PO$_4$/16 mM NaOAc (pH=6.6) (B), 15 mM NaH$_2$PO$_4$/120.2 mM NaOAc (pH=6.6) (C), and 100 mM NaH$_2$PO$_4$/800 mM NaOAc (pH=6.6) (D).

Separation method: isocratic for 5 minutes with A, followed by a 15 minute linear gradient to 100% B, followed by a 20 minute linear gradient to 100% C, followed by 10 minute linear gradient to 100% D, followed by 30 minutes isocratic with 100% D.

| Retention times (minutes) in Human Cells: | | | | |
|---|---|---|---|---|
| Compound | Unchanged | Mono-phosphate | Diphosphate | Triphosphate |
| (±) -FTC | 5.0 | 39.0 | 55.0 | 68.0 |

Figure 8:
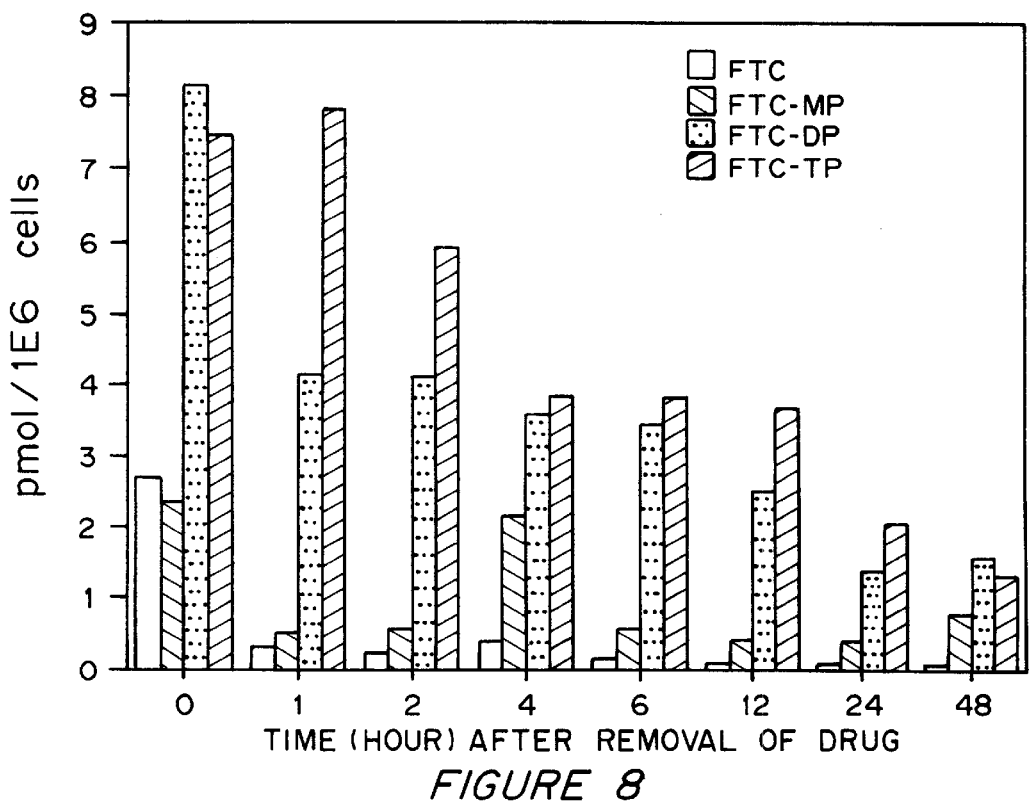
FIG. 8 is a graph of the egress of radiolabeled (±)-FTC from human PBM cells, measured in hours versus pmol/$10^6$ cells.

FIG. 8 is a graph of the egress of radiolabeled (±)-FTC from human PBM cells, measured in hours after drug removal versus concentration (pmol/10$^6$ cells). As indicated in the FIG., FTC-triphosphate has an intracellular half-life of approximately 12 hours and can be easily detected intracellularly at concentrations of 1–5 μM 48 hours after the removal of the extracellular drug, which is well above the EC$_{50}$ for the compound. Further, the affinity (K$^I$) for (±)-FTC triphosphate using HIV RT is 0.2 μM, which is below the 48 hour concentration level.

EXAMPLE 12

Anti-HIV Activity of Pharmaceutically Acceptable Derivatives of (±)-PTC a. A number of pharmaceutically acceptable derivatives of (±)-FTC prepared by derivatizing the 5'and N$^4$ positions were evaluated for anti-HIV activity in PBM cells using a procedure similar to that described in Example 6. The results are as follows. The 5'-O-butyrate ester of (±)-FTC exhibited an EC$_{50}$ of 0.0017. The N$^4$-acetyl derivative of (±)-FTC exhibited an EC$_{50}$ of 0.0028. The 5'-O-butyrate, N$^4$-ester of (±)-FTC exhibited an EC$_{50}$ =0.0058.

b. The anti-HIV activity of the 5'-O-butyrate ester of (±)-FTC in the MT4 system (EC$_{50}$) was 0.04 μM. In the same assay, the unacylated (±)-FTC exhibited an IC50 of 0.52 μM. The IC50 for AZT in this system was 0.09 μM.

V. Ability of FTC to Inhibit the Replication of HBV

EXAMPLE 13

Evaluation of Activity of (+) and (−)-Enantiomers of FTC in 2.2.15 Cell Cultures The ability of the enantiomers of FTC to inhibit the growth of virus in 2.2.15 cell cultures (HepG2 cells transformed with hepatitis virion) is described in detail below.

A summary and description of the assay for antiviral effects in this culture system and the analysis of HBV DNA has been described (Korba and Milman, 1991, *Antiviral Res.*, 15:217). The antiviral evaluations were performed on two separate passages of cells. All wells, in all plates, were seeded at the same density and at the same time.

Assay Parameters

Due to the inherent variations in the levels of both intracellular and extracellular HBV DNA, only depressions greater than 3.5-fold (for HBV virion DNA) or 3.0-fold (for HBV DNA replication intermediates) from the average levels for these HBV DNA forms in untreated cells are considered to be statistically significant [P<0.05]. The levels of integrated HBV DNA in each cellular DNA preparation (which remain constant on a per cell basis in these experiments) were used to calculate the levels of intracellular HBV DNA forms, thereby ensuring that equal amounts of cellular DNA were compared between separate samples.

Typical values for extracellular HBV virion DNA in untreated cells ranged from 50 to 150 pg/ml culture medium (average of approximately 76 pg/ml). Intracellular HBV DNA replication intermediates in untreated cells ranged from 50 to 100 pg/μg cell DNA (average approximately 74 pg/μg cell DNA). In general, depressions in the levels of intracellular HBV DNA due to treatment with antiviral compounds are less pronounced, and occur more slowly, than depressions in the levels of HBV virion DNA (Korba and Milman, 1991, *Antiviral Res.*, 15:217).

The manner in which the hybridization analyses were performed for these experiments resulted in an equivalence of approximately 1.0 pg of intracellular HBV DNA to 2–3 genomic copies per cell and 1.0 pg/ml of extracellular HBV DNA to 3×10$^5$ viral particles/ml.

Toxicity Analysis

Toxicity analyses were performed to assess whether any observed antiviral effects were due to a general effect on cell viability. The method used herein was the measurement of the uptake of neutral red dye, a standard and widely used assay for cell viability in a variety of virus-host systems, including HSV and HIV. Toxicity analyses were performed in 96-well flat bottomed tissue culture plates. Cells for the toxicity analyses were cultured and treated with test compounds with the same schedule as described for the antiviral evaluations below. Each compound was tested at 4 concentrations, each in triplicate cultures (wells "A", "B", and "C"). Uptake of neutral red dye was used to determine the relative level of toxicity. The absorbance of internalized dye at 510 nm (A$_{sin}$) was used for the quantitative analysis. Values are presented as a percentage of the average A$_{sin}$ values in 9 separate cultures of untreated cells maintained on the same 96-well plate as the test compounds. Dye uptake in the 9 control cultures on plate 5 ranged from 91.6% to 110.4%, and on plate 6 from 96.6% to 109%. The results are provided in Table 6.

TABLE 6

Toxicity Analysis of Test Compounds in 2.2.15 Cells

| | | CONC. | DYE UPTAKE (% OF CONTROL) | | |
|---|---|---|---|---|---|
| PLATE | COMPOUND | (μM) | WELL A | WELL B | WELL C |
| 5 | DMSO | 10.0* | 0.7 | 1.6 | 0.9 |
| | | 3.3 | 55.9 | 68.7 | 61.7 |
| | | 1.0 | 91.2 | 96.4 | 106.8 |
| | | 0.3 | 98.7 | 102.9 | 93.5 |
| 6 | (−) -FTC | 300 | 53.0 | 51.1 | 51.5 |
| | | 100 | 64.1 | 66.6 | 77.6 |
| | | 30 | 98.7 | 94.3 | 96.4 |
| | | 10 | 94.3 | 94.9 | 92.2 |
| 6 | (+) -FTC | 300 | 43.4 | 56.7 | 58.5 |
| | | 100 | 77.7 | 66.3 | 72.1 |
| | | 30 | 81.1 | 88.3 | 88.1 |
| | | 10 | 90.9 | 99.4 | 90.5 |

*For DMSO, concentrations are presented as percent of original stock solution.

Toxicity Evaluation

As indicated in Table 6, no significant toxicity (greater than 50% depression of the dye uptake levels observed in untreated cells) was observed for the test compounds at the concentrations used for the antiviral evaluations. Both test compounds, (−)-FTC and (+)-FTC, appeared to be toxic at the highest concentration used for the toxicity tests (330 $\mu$M).

Antiviral Evaluations

Controls

Within normal variations, levels of HBV virion DNA and intracellular HBV replication intermediates [HBV RI] remained constant in the untreated cells over the challenge period. DMSO, at a concentration of 1%, did not affect the levels of HBV replication in 2.2.15 cell cultures.

Test Compounds

As indicated in Table 7, both (−)-FTC and (+)-FTC significantly inhibited the replication of HBV at the tested levels. As indicated in Table 8, (−)-FTC still significantly inhibits the synthesis of HBV virion DNA and intracellular HBV DNA at concentrations of 4, 1, and 0.25 $\mu$M.

TABLE 7

Effect of Test Compounds on HBV Production In 2.2.15 Cell Cultures

| WELL | TREATMENT | HBV Virion DNA* (pg/ml Culture Medium) | | | Intracellular HBV DNA (pg/ug Cell DNA) | |
|---|---|---|---|---|---|---|
| | | DAY 0 | DAY 4 | DAY 9 | MONO. | RI |
| 7A | Untreated Cells | 59 | 75 | 94 | 2.7 | 93 |
| 7B | Untreated Cells | 47 | 64 | 88 | 2.5 | 93 |
| 8A | Untreated Cells | 65 | 100 | 71 | 2.2 | 97 |
| 8B | Untreated Cells | 77 | 65 | 110 | 2.4 | 62 |
| 7K | DMSO @ 1.00% | 100 | 50 | 48 | 1.9 | 95 |
| 7L | DMSO @ 1.00% | 48 | 96 | 54 | 2.8 | 98 |
| 8K | DMSO @ 1.00% | 93 | 63 | 68 | 2.2 | 86 |
| 8L | DMSO @ 1.00% | 66 | 57 | 59 | 1.6 | 97 |
| 9U | (−) −FTC @ 10 $\mu$M | 120 | 36 | 1 | 1.1 | 14 |
| 9V | (−) −FTC 10 $\mu$M | 89 | 48 | 1 | 1.5 | 19 |
| 10U | (−) −FTC 10 $\mu$M | 58 | 41 | 0.1 | 1.9 | 13 |
| 10V | (−) −FTC 10 $\mu$M | 110 | 32 | 0.1 | 1.2 | 16 |
| 9W | (+) −FTC @ 10 $\mu$M | 88 | 42 | 0.1 | 0.8 | 14 |
| 9X | (+) −FTC 10 $\mu$M | 58 | 57 | 0.2 | 0.4 | 19 |
| 10W | (+) −FTC 10 $\mu$M | 69 | 55 | 0.1 | 0.7 | 17 |
| 10X | (+) −FTC 10 $\mu$M | 45 | 39 | 0.1 | 0.4 | 15 |

*Sensitivity cutoff for HBV virion DNA was 0.1 pg/ml.
@ Intracellular HBV DNA was analyzed 24 hours following the 9th day of treatment. The levels of integrated HBV DNA in each cell DNA preparation were used to calculate the levels of episomal 3.2 Kb HBV genomes (MONO.) and HBV DNA replication intermediates (RI).

TABLE 8

Effect of Test Compounds on KBV Production in 2.2.15 Cell Cultures

| WELL | TREATMENT | HBV VIRION DNA* (pg/ml CULTURE MEDIUM) | | | INTRACELLULAR HBV DNA* (pg/$\mu$g CELL DNA) | |
|---|---|---|---|---|---|---|
| | | DAY 0 | DAY 4 | DAY 9 | MONO. | RI |
| 31A | untreated cells | 64 | 54 | 65 | 2.8 | 65 |
| 31B | " | 51 | 54 | 77 | 2.0 | 53 |
| 32A | " | 100 | 76 | 56 | 3.5 | 81 |
| 32B | " | 53 | 97 | 83 | 3.1 | 68 |
| 35A | (−) −FTC @ 4 $\mu$M | 74 | 27 | >0.1 | 1.4 | 1 |
| 35B | " | 87 | 28 | >0.1 | 0.5 | 1 |
| 36A | " | 120 | 20 | 1 | 0.9 | 1 |
| 36B | " | 59 | 16 | 0.2 | 0.2 | 2 |
| 35C | (−) −FTC @ 1 $\mu$M | 70 | 13 | >0.1 | 1.7 | 2 |
| 35D | " | 62 | 15 | >0.1 | 1.2 | 3 |
| 36C | " | 60 | 22 | 1 | 1.4 | 2 |
| 36D | " | 89 | 28 | 0.3 | 1.5 | 4 |
| 35E | (−) −FTC @ 0.25 $\mu$M | 84 | 15 | >0.1 | 1.5 | 4 |
| 35F | " | 89 | 16 | 4 | 2.2 | 4 |
| 36E | " | 66 | 13 | 1 | 1.8 | 8 |
| 36F | " | 49 | 19 | 0.1 | 0.3 | 9 |

*Sensitivity cutoff for HBV virion DNA was 0.1 pg/ml.
+ Analysis of intracellular HBV DNA was 24 hours following the 9th day of treatment. The levels of integrated HBV DNA in each cell DNA preparation were used to calculate the levels of episomal 3.2 kb HBV genomes (MONO.) and HBV DNA replication intermediates (RI).

EXAMPLE 14

Uptake of (±)-FTC into Human Liver Cells; HVB Activity of FTC

Figure 9:
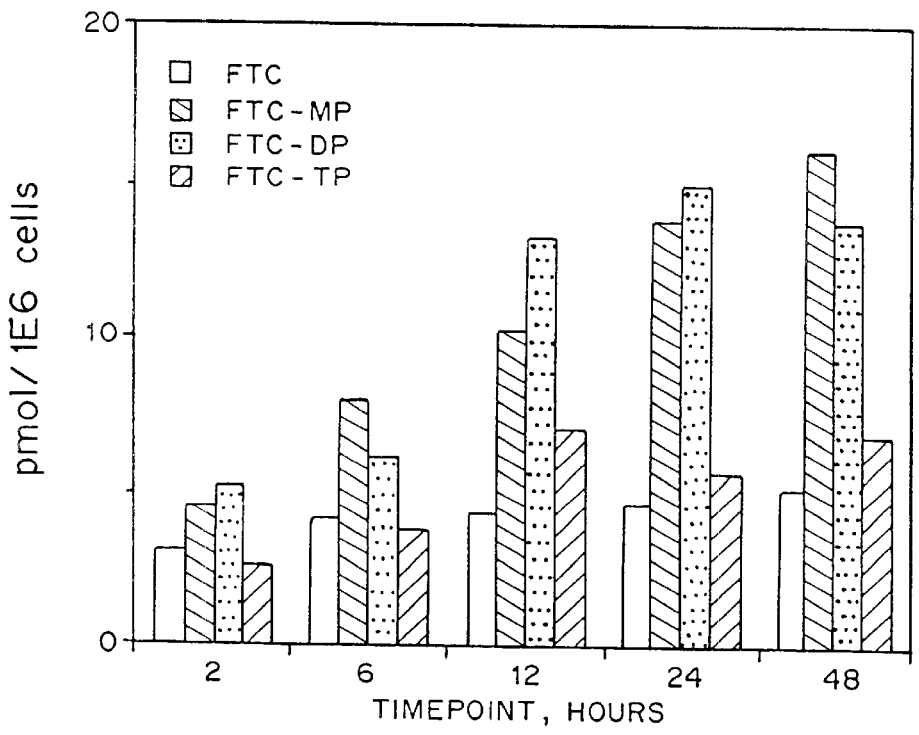
FIG. 9 illustrates the presence of [$^3$H]-(±)-FTC and its phosphorylated derivatives in human HepG-2 cells (average of two determinations) incubated in media containing 10 $\mu$M [$^3$H]-(±)-FTC, measured in pmol/$10^6$ cells over time.

The procedure of Example 9 was repeated with human liver cells (HepG2 cells, available from the ATCC) to determine the uptake and metabolism of FTC in these cells. As shown in FIG. 9, (±)-FTC is taken up by HepG2 cells in large amounts. These human liver cells metabolize a large percentage of the (±)-FTC to (±)-FTC triphosphate.

This data, in conjunction with other data provided herein, indicate that (±)-FTC, as well as its (−) and (+) enantiomers, are phosphorylated in liver cells. These cells can be transformed with hepatitis B virus.

EXAMPLE 15

Egress of FTC in Human HepG2 Cells

Figure 10:
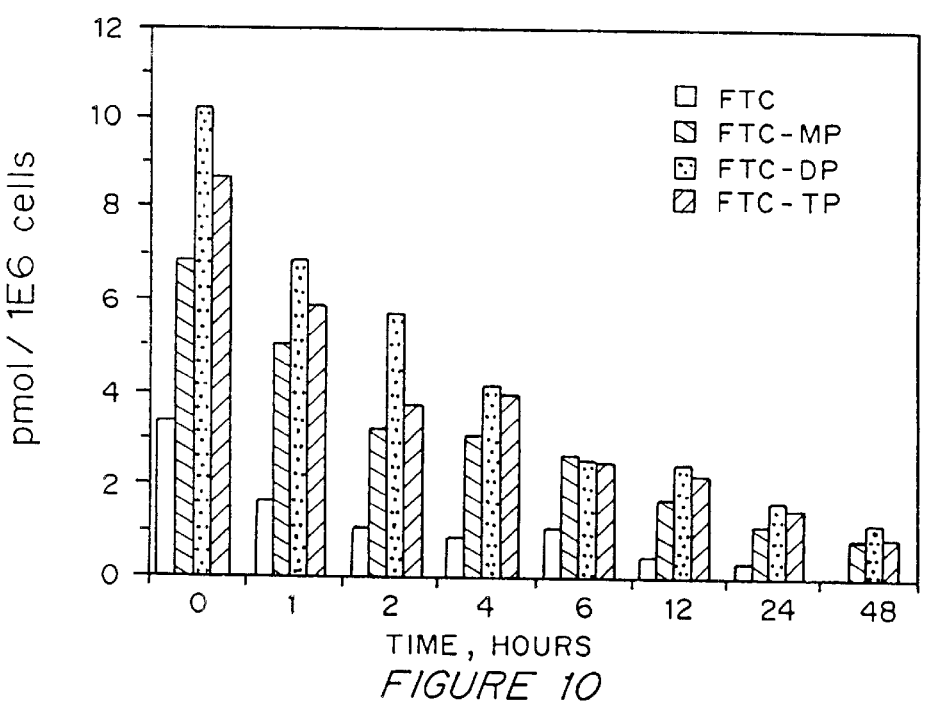
FIG. 10 illustrates the egress of [$^3$H]-(±)-FTC and its phosphorylated derivatives in human HepG2 in pmol/$10^6$ cells over time cells after pulsing cells with 10 $\mu$M [$^3$H]-(±)-FTC (700 DPM/pmole) for 24 hours, and evaluating the concentration of compound 24 hours after removal.

FIG. 10 illustrates the egress of [$^3$H]-(±)-FTC and its phosphorylated derivatives in human HepG2 in pmol/$10^6$ cells over time cells after pulsing cells with 10 μM [$^3$H]-(±)-FTC (700 DPM/pmole) for 24 hours, and evaluating the concentration of compound 24 hours after removal.

Figure 11:
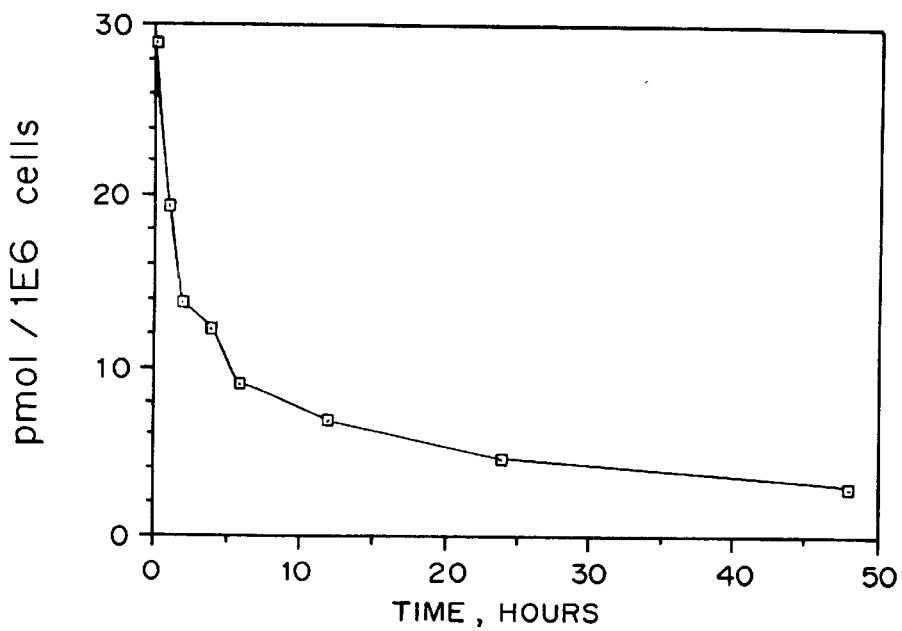
FIG. 11 illustrates the decrease in the combined concentration of [$^3$H]-(±)-FTC and its phosphorylated derivatives from human HepG2 cells after incubation with 10 $\mu$M [$^3$H]-(±)-FTC (700 DPM/pmole) for 24 hours, in pmol/$10^6$ cells over time.

FIG. 11 illustrates the decrease in the combined concentration of [$^3$H]-(±)-FTC and its phosphorylated derivatives from human HepG2 cells after incubation with 10 μM [$^3$H]-(±)-FTC (700 DPM/pmole) for 24 hours, in pmol/$10^6$ cells over time.

As illustrated, even at 48 hours, over 1 μM of active compound (which is significantly higher than the $EC_{50}$ for the compound) is still present in the cells.

V. Toxicity in Granulocyte-Macrophage Precursor Cells

EXAMPLE 16

Effect of FTC on Colony Formation of Granulocyte-Macrophage Precursor Cells

Figure 12:
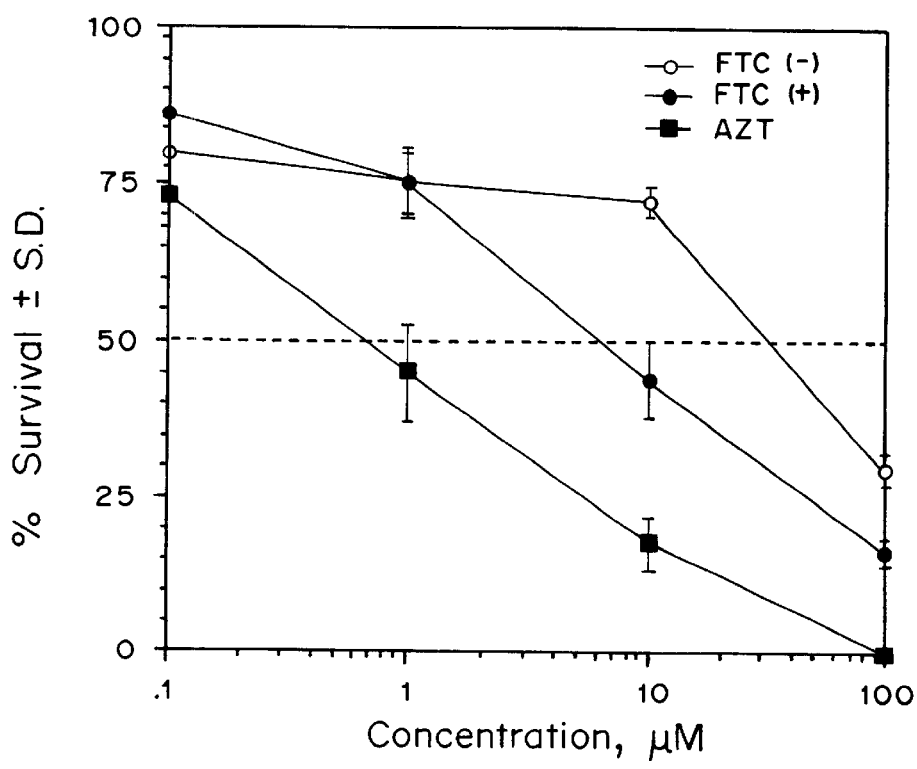
FIG. 12 is a graph of the effect of the enantiomers of FTC on colony formation of granulocyte-macrophage precursor cells, as measured in percent survival versus concentration in $\mu$M ((−)-FTC, open circle; (+)-FTC, darkened circle; AZT, darkened square.

FIG. 12 is a graph of the effect of the (−) and (+) enantiomers of FTC on colony formation of granulocytes-macrophage precursor cells, as measured in percent survival versus concentration in μM ((−)-FTC, open circle; (+)-FTC, darkened circle; AZT, darkened square. As indicated, the (−)-enantiomer of FTC appears to be less toxic i.e., have a higher $IC_{50}$, than either the (+)-enantiomer or AZT in this cell line.

VI. Pharmacokinetics of FTC

EXAMPLE 17

Metabolism of FTC on Administration to Rats (±)-FTC was administered intravenously at dosages of 10, 50 and 100 mg/kg to rats, and the area under the plasma drug concentration versus time (AUC), total clearance ($CL_T$), steady-state volume of distribution ($V_{SS}$), mean residence time (MRT) and half-life ($t_{1/2}$), evaluated. The results are provided in Table 9.

TABLE 9

Pharmacokinetic Parameters of FTC After Intravenous Administration of 10, 50, 100 mg/kg to Rats*

| Dose mg/kg | AUC mg h/L | $CL_T$ L/h/kg | $V_{SS}$ L/kg | MRT h | $t_{1/2}$ h |
|---|---|---|---|---|---|
| 10 | 9.65 | 0.988 | 0.758 | 0.768 | 0.757 |
| 50 | 57.11 | 0.874 | 0.699 | 0.800 | 0.815 |
| 100 | 120.72 | 0.830 | 0.663 | 0.798 | 0.969 |

*AUC = area under the plasma drug concentration versus time curve;
CL = total clearance;
$V_{SS}$ = steady-state volume of distribution;
MRT = mean residence time;
and $t_{1/2}$ = half-life.

EXAMPLE 18

Pharmacokinetic Parameters for FTC After Intravenous and Oral Administration of FTC Model-independent pharmacokinetic parameters were derived for (±)-FTC by administration (intravenous (I.V.) and oral (P.O.)) of 33.3 mg/kg to Rhesus Monkeys. The results are provided in Table 10. Importantly, the mean bioavailability of the compound in monkeys was 73% (±6).

TABLE 10

Model-Independent Pharmacokinetic Parameters Derived for FTC After Intravenous (I.V.) or Oral (P.O.) Administration of 33.3 mg/kg to Rhesus Monkeys*

| Monkey | AUC mg h/L | $CL_T$ L/h/kg | $V_{SS}$ L/kg | MRT h | $t_{1/2}$ h | $Ka_1$ h⁻ | F % |
|---|---|---|---|---|---|---|---|
| I.V. | | | | | | | |
| RUh | 19.14 | 1.74 | 2.71 | 1.56 | 1.28 | | |
| RMi | 26.31 | 1.26 | 1.97 | 1.56 | 1.22 | | |
| RJd | 22.51 | 1.48 | 2.00 | 1.36 | 1.47 | | |
| Mean ± | 22.65 | 1.49 | 2.23 | 1.49 | 1.32 | | |
| S.D. | 3.59 | 0.24 | 0.42 | 0.12 | 0.13 | | |
| P.O. | | | | | | | |
| RUh | 13.21 | | | 2.07 | 1.58 | 0.48 | 71 |
| RMi | 21.11 | | | 2.32 | 1.08 | 0.43 | 80 |
| RJd | 15.29 | | | 3.23 | 1.47 | 0.31 | 68 |
| Mean ± | 16.54 | | | 2.54 | 1.38 | 0.41 | 73.00 (±6) |
| S.D. | 4.09 | | | 0.61 | 0.26 | 0.09 | 6.24 |

*AUC = area under the plasma drug concentration versus time curve;
CL = total clearance;
$V_{SS}$ = steady-state volume of distribution;
MRT = mean residence time;
and $t_{1/2}$ = half-life;
F = bioavailability;
and $K_a$ = first order absorption rate constant.

TABLE 11

CSF/Serum Ratio of FTC and Its Deaminated Metabolite 1 Hour After Treatment

| Monkey | Route | FTC | Metabolite (FTU) |
|---|---|---|---|
| RUh | I.V. | 0.076 | 0.024 |
| RMi | I.V. | 0.062 | 0.032 |
| RJd | I.V. | 0.162 | 0.052 |
| Mean ± | | 0.100 | 0.036 |
| S.D. | | 0.054 | 0.014 |
| RUh | P.O. | 0.048 | 0.026 |
| RMi | P.O. | 0.039 | 0.037 |
| RJd | P.O. | 0.117 | 0.055 |

TABLE 11-continued

CSF/Serum Ratio of FTC and Its Deaminated Metabolite
1 Hour After Treatment

| Monkey | Route | FTC | Metabolite (FTU) |
| --- | --- | --- | --- |
| Mean ± S.D. | | 0.068 0.043 | 0.039 0.015 |

EXAMPLE 19

CSF/Serum Ratio of FTC and its Metabolites in Rhesus Monkeys

The ability of (±)-FTC to cross the blood-brain barrier was evaluated by administering 33.3 mg/kg of the active compound to rhesus monkeys, and measuring the amount of (±)-FTC in the cerebral spinal fluid (CSF) and blood serum one hour after administration. The results are provided in Table 11. The data indicates that a significant amount of active compound passes through the blood-brain barrier in this mammal.

III. Preparation of Pharmaceutical Compositions

Humans suffering from diseases caused by HIV or HBV infection can be treated by administering to the patient an effective amount of (±)-FTC, or its (−) or (+) enantiomer or a pharmaceutically acceptable derivative or salt thereof in the presence of a pharmaceutically acceptable carrier or diluent. The active materials can be administered by any appropriate route, for example, orally, parenterally, intravenously, intradermally, subcutaneously, or topically, in liquid or solid form.

The active compound is included in the pharmaceutically acceptable carrier or diluent in an amount sufficient to deliver to a patient a therapeutically effective amount of compound to inhibit viral replication in vivo, especially HIV and HBV replication, without causing serious toxic effects in the patient treated. By "inhibitory amount" is meant an amount of active ingredient sufficient to exert an inhibitory effect as measured by, for example, an assay such as the ones described herein.

A preferred dose of (−), (+), or (±)-FTC for all of the above-mentioned conditions will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable derivatives can be calculated based on the weight of the parent nucleoside to be delivered. If the derivative exhibits activity in itself, the effective dosage can be estimated as above using the weight of the derivative, or by other means known to those skilled in the art.

The compound is conveniently administered in unit any suitable dosage form, including but not limited to one containing 7 to 3000 mg, preferably 70 to 1400 mg of active ingredient per unit dosage form. A oral dosage of 50–1000 mg is usually convenient.

Ideally the active ingredient should be administered to achieve peak plasma concentrations of the active compound of from about 0.2 to 70 $\mu$M, preferably about 1.0 to 10 $\mu$M. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

(±)-FTC, or its (−) or (+)-enantiomer or pharmaceutically acceptable salts thereof can be administered as a component of an elixir, suspension, syrup, wafer, chewing gum or the like. A syrup may contain, in addition to the active compounds, sucrose as a sweetening agent and certain preservatives, dyes and colorings and flavors.

(±)-FTC, or its (−) or (+)-enantiomers, or pharmaceutically acceptable derivatives or salts thereof can also be mixed with other active materials that do not impair the desired action, or with materials that supplement the desired action, such as antibiotics, antifungals, antiinflammatories, or other antivirals, including other nucleoside anti-HIV compounds.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

IV. Preparation of Phosphate Derivatives of FTC

Mono, di, and triphosphate derivative of FTC can be prepared as described below.

The monophosphate can be prepared according to the procedure of Imai et al., *J. Org. Chem.*, 34(6), 1547–1550 (June 1969). For example, about 100 mg of FTC and about 280 $\mu$l of phosphoryl chloride are reacted with stirring in about 8 ml of dry ethyl acetate at about 0° C. for about four hours. The reaction is quenched with ice. The aqueous phase is purified on an activated charcoal column, eluting with 5% ammonium hydroxide in a 1:1 mixture of ethanol and water. Evaporation of the eluant gives ammonium FTC-5'-monophosphate.

The diphosphate can be prepared according to the procedure of Davisson et al., *J. Org. Chem.*, 52(9), 1794–1801 (1987). FTC diphosphate can be prepared from the corresponding tosylate, that can be prepared, for example, by reacting the nucleoside with tosyl chloride in pyridine at room temperature for about 24 hours, working up the product in the usual manner (e.g., by washing, drying, and crystallizing it).

The triphosphate can be prepared according to the procedure of Hoard et al., *J. Am. Chem. Soc.*, 87(8), 1785–1788 (1965). For FTC is activated (by making a imidazolide, according to methods known to those skilled in the art) and treating with tributyl ammonium pyrophosphate in DMF. The reaction gives primarily the triphosphate of the nucleoside, with some unreacted monophosphate and some diphosphate. Purification by anion exchange chromatography of a DEAE column is followed by isolation of the triphosphate, e.g., as the tetrasodium salt.

This invention has been described with reference to its preferred embodiments. Variations and modifications of the invention, will be obvious to those skilled in the art from the foregoing detailed description of the invention. It is intended that all of these variations and modifications be included within the scope of the appended claims.

We claim:

1. A method for treating HIV infection in humans comprising administering an effective amount of (−)-β-L-2-hydroxymethyl-5-(5-fluorocytosin-1-yl)-1,3-oxathiolane, or its physiologically acceptable salt, optionally in a pharmaceutically acceptable carrier.

2. The method of claim 1, wherein the carrier is suitable for oral delivery.

3. The method of claim 1, wherein the carrier comprises a capsule.

4. The method of claim 1, wherein the carrier is in the form of a tablet.

5. The method of claim 1, wherein the administration is parenteral.

6. The method of claim 1, wherein β-L-2-hydroxymethyl-5-(5-fluorocytosin-1-yl)-1,3-oxathiolane is administered in a form that is at least 95% free of its corresponding β-D-enantiomer.

7. The method of claim 1, wherein β-L-2-hydroxymethyl-5-(5-fluorocytosin-1-yl)-1,3-oxathiolane is administered in a form that is at least 95% free of its corresponding β-D-enantiomer.

8. The method of claim 1, wherein β-L-2-hydroxymethyl-5-(5-fluorocytosin-1-yl)-1,3-oxathiolane is administered as an isolated enantiomer.

9. A method for treating HIV infection in humans comprising administering an effective amount of (+)-β-D-2-hydroxymethyl-5-(5-fluorocytosin-1-yl)-1,3-oxathiolane, or its physiologically acceptable salt, optionally in a pharmaceutically acceptable carrier.

10. The method of claim 9, wherein the carrier is suitable for oral delivery.

11. The method of claim 9, wherein the carrier comprises a capsule.

12. The method of claim 9, wherein the carrier is in the form of a tablet.

13. The method of claim 9, wherein the administration is parenteral.

14. The method of claim 9, wherein β-D-2-hydroxymethyl-5-(5-fluorocytosin- 1-yl)-1,3-oxathiolane is administered in a form that is at least 95% free of its corresponding β-L enantiomer.

15. The method of claim 9, wherein β-D-2-hydroxymethyl-5-(5-fluorocytosin-1-yl)-1,3-oxathiolane is administered in a form that is at least 95% free of its corresponding β-L-enantiomer.

16. The method of claim 9, wherein β-D-2-hydroxymethyl-5-(5-fluorocytosin-1-yl)-1,3-oxathiolane is administered as an isolated enantiomer.

17. A method for treating HIV infection in humans comprising administering an effective amount of the monphosphate, diphosphate or triphosphate of β-L-2-hydroxymethyl-5-(5-fluorocytosin-1-yl)-1,3-oxathiolane, or its physiologically acceptable salt, optionally in a pharmaceutically acceptable carrier.

18. The method of claim 17, wherein the phosphate of β-L-2-hydroxymethyl-5-(5-fluorocytosin-1-yl)-1,3-oxathiolane is administered in a form that is at least 95% free of its corresponding β-D-enantiomer.

19. The method of claim 17, wherein the phosphate of β-L-2-hydroxymethyl-5-(5-fluorocytosin-1-yl)-1,3-oxathiolane is administered as an isolated enantiomer.

20. A method for treating HIV infection in humans comprising administering an effective amount of the monophosphate, diphosphate, or triphosphate of β-D-2-hydroxymethyl-5-(5-fluorocytosin-1-yl)-1,3-oxathiolane, or its physiologically acceptable salt, optionally in a pharmaceutically acceptable carrier.

21. The method of claim 20, wherein the phosphate of β-D-2-hydroxymethyl-5-(5-fluorocytosin-1-yl)-1,3-oxathiolane is administered in a form that is at least 95% free of its corresponding β-L-enantiomer.

22. The method of claim 20, wherein the phosphate of β-D-2-hydroxymethyl-5-(5-fluorocytosin-1-yl)-1,3-oxathiolane is administered as an isolated enantiomer.

* * * * *